US007314968B2

(12) United States Patent
Moon et al.

(10) Patent No.: US 7,314,968 B2
(45) Date of Patent: Jan. 1, 2008

(54) TRANSGENIC FISH AND β-CATENIN SIGNALING PATHWAY MODEL

(75) Inventors: Randall T. Moon, Kenmore, WA (US); Richard I. Dorsky, Salt Lake City, UT (US)

(73) Assignee: University of Washington, Seattle, WA (US)

( * ) Notice: Subject to any disclaimer, the term of this patent is extended or adjusted under 35 U.S.C. 154(b) by 431 days.

(21) Appl. No.: 10/679,191

(22) Filed: Oct. 3, 2003

(65) Prior Publication Data

US 2004/0168210 A1 Aug. 26, 2004

Related U.S. Application Data

(60) Provisional application No. 60/416,504, filed on Oct. 3, 2002.

(51) Int. Cl.
*A01K 67/027* (2006.01)
*G01N 33/00* (2006.01)
*C12N 15/01* (2006.01)
*C12N 15/00* (2006.01)

(52) U.S. Cl. .................. 800/20; 435/320.1; 800/3; 800/21

(58) Field of Classification Search .............. None
See application file for complete search history.

(56) References Cited

U.S. PATENT DOCUMENTS 5,223,409 A 6/1993 Ladner et al.
6,130,313 A * 10/2000 Li et al. .................. 530/324

OTHER PUBLICATIONS

Dorsky et al. A transgenic Lef1/beta-catenin-dependent reporter is expressed in spatially☐☐restricted domains throughout zebrafish development.☐☐Dev Biol. Jan. 15, 2002;241(2):229-37.*
Talbot et al. Zebrafish mutations and functional analysis of the vertebrate genome.☐☐Genes Dev. Apr. 1, 2000;14(7):755-62.*
Pietrzkowski et al. Characterization of an enhancer-like structure in the promoter region of the ☐☐proliferating cell nuclear antigen (PCNA) gene.☐☐Exp Cell Res. Apr. 1991;193(2):283-90.*
Chan et al. Promoter analysis of the nuclear gene encoding the chloroplast☐☐glyceraldehyde-3-phosphate dehydrogenase B subunit of *Arabidopsis thaliana*.☐☐Plant Mol Biol. May 2001;46(2):131-41.*
Omilli et al. Sequences involved in initiation of simian virus 40 late transcription in the absence of T antigen. Mol Cell Biol. Jun. 1986;6(6):1875-85.*
Arnone et al. The hardwiring of development: organization and function of genomic regulatory systems. Development. May 1997;124(10):1851-64.*
pcDNA/Neo Vector, Datasheet[online], Invitrogen Life Technol, [retrieved on May 7, 2007]. Retrieved from the Internet: URL: www.invitrogen.com/content/sfs/vectors/pcdna1neo.pdf.*

Allen, N.D., et al., "Transgenes as Probes for Active Chromosomal Domains in Mouse Development," *Nature* 333(6176):852-855, Jun. 30, 1988.
Amsterdam, A., and N. Hopkins, "Retrovirus-Mediated Insertional Mutagenesis in Zebrafish," *Methods in Cell Biol.* 60:87-98, 1999.
Bernhardt, R.R., et al, "Identification of Spinal Neurons in the Embryonic and Larval Zebrafish," *J. Comp. Neurol.* 302:603-616, 1990.
Billin, A.N., et al., "β-Catenin-Histone Deacetylase Interactions Regulate the Transition of LEF1 From a Transcriptional Repressor to an Activator," *Mol. Cell. Biol.* 20(18):6882-6890, Sep. 2000.
Perrimon, N., and M. Boutros, "*Drosophila* Wnt/Fz Pathways," *Science's STKE* (Connections Map, as seen in May 2002). <http://stke.sciencemag.org/cgi/cm/stkecm;CMP_6459>.
Bowerman, B., "*C. elegans* T Cell Polarity Wnt Pathway," *Science's STKE* (Connections Map, as seen Mar. 2004), at least as early as May 2002. <http://stke.sciencemag.org/cgi/cm/stkecm;CMP_10440>.
Bowerman, B., "*C. elegans* Gonadogenesis Wnt Pathway," *Science's STKE* (Connections Map, as seen Mar. 2004), at least as early as May 2002. <http://stke.sciencemag.org/cgi/cm/stkecm;CMP_10698>.
Bowerman, B., "*C. elegans* Endoderm Induction Wnt Pathway," *Science's STKE* (Connections Map, as seen Mar. 2004), at least as early as May 2002. <http://stke.sciencemag.org/cgi/cm/stkecm;CMP_6104>.
Bowerman, B., "*C. elegans* QL Neuroblast Migration Wnt Pathway," *Science's STKE* (Connections Map, as seen Mar. 2004), at least as early as May 2002. <http://stke.sciencemag.org/cgi/cm/stkecm;CMP_9763>.
Brannon, M., et al., "XCtBP is a XTcf-3 Co-Repressor With Roles Throughout *Xenopus* Development," *Development* 126:3159-3170, 1999.
Brannon, M., et al., "A β-Catenin/XTcf-3 Complex Binds to the *Siamois* Promoter to Regulate Dorsal Axis Specification in *Xenopus*," *Genes Dev.* 11:2359-2370, 1997.
Bunin, B.A., and J.A. Ellman, "A General and Expedient Method for the Solid-Phase Synthesis of 1,4-Benzodiazepine Derivatives," *J. Am. Chem. Soc.* 114:10997-10998, Dec. 1992.
Burgess, S., and N. Hopkins, "Use of Pseudotyped Retroviruses in Zebrafish as Genetic Tags," *Methods Enzymol.* 327:145-161, 2000.
Carell, T., et al., "A Novel Procedure for the Synthesis of Libraries Containing Small Organic Molecules," *Angew. Chem Int. Ed. Engl.* 33(20):2059-2061, 1994.
Carell, T., et al., "A Solution-Phase Screening Procedure for the Isolation of Active Compounds from a Library of Molecules," *Angew. Chem. Int. Ed. Engl.* 33(20):2061-2064, 1994.

(Continued)

*Primary Examiner*—Daniel M Sullivan
(74) *Attorney, Agent, or Firm*—Christensen O'Connor Johnson Kindness PLLC

(57) ABSTRACT

The present invention is directed a Lef1/β-catenin-dependent reporter and to transgenic fish containing this reporter. The present invention is also directed to the use of the reporter and the transgenic fish as a model for the β-catenin signaling pathway. The model is useful for identifying genes in the β-catenin signaling pathway and for identifying drugs that can modulate the β-catenin signaling pathway. Such drugs are useful for treating or preventing melanoma, colorectal cancer and osteoporosis, among other disease conditions.

4 Claims, 12 Drawing Sheets

OTHER PUBLICATIONS

Christian, J.L., et al., "*Xwnt*-8, a *Xenopus Wnt*-1/*int*-1-Related Gene Responsive to Mesoderm-Inducing Growth Factors, May Play a Role in Ventral Mesodermal Patterning During Embryogenesis," *Development 111*:1045-1055, 1991.

Cho, C.Y., et al., "An Unnatural Biopolymer," *Science 261*:1303-1305, Sep. 3, 1993. <<http://links.jstor.org/sici?sici=0036-8075%2819930903%3A261%3A5126%3C1303%3AAUB%3E2.0.CO%3B2-5>.

Cull, M.G., et al., "Screening for Receptor Ligands Using Large Libraries of Peptides Linked to the C Terminus of the lac Repressor," *Proc. Natl. Acad. Sci. USA 89*(5):1865-1869, Mar. 1, 1992. <<http://links.jstor.org/sici?sici=0027-8424%2819920301%2989%3A5%3C1865%3ASFRLUL%3E2.0.CO%3B2-2>.

Culp, P., et al., "High-Frequency Germ-Line Transmission of Plasmid DNA Sequences Injected Into Fertilized Zebrafish Eggs," *Proc. Natl. Acad. Sci. USA 88*(18):7953-7957, Sep. 15, 1991. <<http://links.jstor.org/sici?sici=0027-8424%2819910915%2988%3A18%3C7953%3AHGTOPD%3E2.0.CO%3B2-T>.

Cwirla, S.E., et al., *Proc. Natl. Acad. Sci. USA 87*(16):6378-6382, Aug. 1990. <<http://links.jstor.org/sici?sici=0027-8424%28199008%2987%3A16%3C6378%3APOPAVL%3E2.0.CO%3B2-3>.

Devlin, J.J., et al., "Random Peptide Libraries: A Source of Specific Protein Binding Molecules," *Science 249*(4967):404-406, Jul. 27, 1990. <<http://links.jstor.org/sici?sici=0036-8075%2819900727%293%3A249%3A4967%3C404%3ARPLASO%E2.0/CO%3B2-4>.

De Witt, S.H., et al., "Diversomers': An Approach to Nonpeptide Nonoligomeric Chemical Diversity," *Proc. Natl. Acad. Sci. USA 90*(15):6909-6913, Aug. 1, 1993. <<http://links.jstor.org/sici?sici=0027-8424%2819930801%2990%3A15%3C6909%3A%22AATNN%3E2.0.CO%3B2-3>.

Dickinson, M.E., et al., "Dorsalization of the Neural Tube by the Non-Neural Ectoderm," *Development 121*:2099-2106, 1995.

Dorsky, R.I., et al., "Control of Neural Crest Cell Fate by the Wnt Signalling Pathway," *Nature 396*:370-373, Nov. 26, 1998.

Dorsky, R.I., et al., "Maternal and Embryonic Expression of Zebrafish *lef1*," *Mech. Dev. 86*:147-150, 1999.

Dorsky, R.I., et al., "Direct Regulation of *Nacre*, a Zebrafish *MITF* Homolog Required for Pigment Cell Formation, by the Wnt Pathway," *Genes Dev. 14*:158-162, 2000.

Driever, W., et al., "A Genetic Screen for Mutations Affecting Embryogenesis in Zebrafish," *Development 123*:37-46, 1996.

Eastman, Q., and R. Grosschedl, "Regulation of LEF-1/TCF Transcription Factors by Wnt and Other Signals," *Curr. Opin. Cell Biol. 11*:233-240, 1999.

Erb, E., et al., "Recursive Deconvolution of Combinatorial Chemical Libraries," *Proc. Natl. Acad. Sci. USA 91*(24):11422-11426, Nov. 22, 1994. <<http://links.jstor.org/sici?sici=0027-8424%2819941122%2991%3A24%3C11422%3ARDOCCL%3E2.CO%3B-2-L>.

Felici, F., et al., "Selection of Antibody Ligands From a Large Library of Oligopeptides Expressed on a Multivalent Exposition Vector," *J. Mol. Biol. 222*:301-310, 1991.

Fodor, S.P.A., et al., "Multiplexed Biochemical Assays With Biological Chips," *Nature 364*:555-556, Aug. 5, 1993.

Galceran, J., et al., "*Wnt3a*$^{-/-}$-Like Phenotype and Limb Deficiency in *Lef1*$^{-/-}$*Tcf1*$^{-/-}$ Mice," *Genes Dev. 13*:709-717, 1999.

Gallop, M.A., et al., "Applications of Combinatorial Technologies to Drug Discovery," *J. Med. Chem. 37*(9):1233-1251, Apr. 29, 1994.

Golling, G., et al., "Insertional Mutagenesis in Zebrafish Rapidly Identifies Genes Essential for Early Vertebrate Development," *Nat. Genet. 31*:135-140, Jun. 2002.

Gong, Y., et al., "LDL Receptor-Related Protein 5 (LRP5) Affects Bone Accrual and Eye Development," *Cell 107*:513-523, Nov. 16, 2001.

Gossler, A., et al., "Mouse Embryonic Stem Cells and Reporter Constructs to Detect Developmentally Regulated Genes," *Science*, New Series, 244(4903):463-465, Apr. 28, 1989. <<http://links.jstor.org/sici?sici=0036-8075%2819890428%293%3A244%3A4903%3C463%3AMESCAR%3E2.0.CO%3B2-1>.

Haffter, P., et al., "The Identification of Genes With Unique and Essential Functions in the Development of the Zebrafish, *Danio rerio*," *Development 123*:1-36, 1996.

Halloran, M.C., et al., "Laser-Induced Gene Expression in Specific Cells of Transgenic Zebrafish," *Development 127*:1953-1960, 2000.

Heasman, J., et al., "Overexpression of Cadherins and Underexpression of β-Catenin Inhibit Dorsal Mesoderm Induction in Early *Xenopus* Embryos," *Cell 79*:791-803, Dec. 2, 1994.

Heikkilä, M., et al., "*Wnts* and the Female Reproductive Systems," *J. Exp. Zool. 290*:616-623, 2001.

Hinck, L., et al., "Wnt-1 Modulates Cell-Cell Adhesion in Mammalian Cells by Stabilizing β-Catenin Binding to the Cell Adhesion Protein Cadherin," *J. Cell Biol. 124*(5):729-741, 1994.

Hollyday, M., et al., "*Wnt* Expression Patterns in Chick Embryo Nervous System," *Mech. Dev. 52*:9-25, 1995.

Horwell, D., et al., "Targeted' Molecular Diversity: Design and Development of Non-Peptide Antagonists for Cholecystokinin and Tachykinin Receptors," *Immunopharmacol. 33*:68-72, 1996.

Houghten, R.A., et al., "The Use of Synthetic Peptide Combinatorial Libraries for the Identification of Bioactive Peptides," *BioTechniques 13*(3):412-421, Sep. 1992.

Hug, B., et al., "*tbx6*, a *Brachyury*-Related Gene Expressed by Ventral Mesendodermal Precursors in the Zebrafish Embryo," *Dev. Biol. 183*:61-73, 1997.

Ikeya, M., et al., "Wnt Signalling Required for Expansion of Neural Crest and CNS Progenitors," *Nature 389*:966-970, Oct. 30, 1997.

Imai, Y., et al., "Analysis of Chromosomal Rearrangements Induced by Postmeiotic Mutagenesis With Ethylnitrosourea in Zebrafish," *Genetics 155*:261-272, May 2000.

Inoue, K., et al., "Electroporation as a New Technique for Producing Transgenic Fish," *Cell. Differ. Develop. 29*(2):123-128, 1990.

Ishikawa, T., et al., "Mouse Wnt Receptor Gene *Fzd5* is Essential for Yolk Sac and Placental Angiogenesis," *Development 128*25-33, 2001.

Kelly, C., et al., "Maternally Controlled β-Catenin-Mediated Signaling is Required for Organizer Formation in the Zebrafish," *Development 127*3899-3911, 2000.

Kim, C.-H., et al., "Repressor Activity of Headless/Tcf3 is Essential for Vertebrate Head Formation," *Nature 407*:913-916, Oct. 19, 2000.

Kimmel, C.B., "Genetics and Early Development of Zebrafish," *Trends Genet. 5*(8):283-288, Aug. 1989.

Korinek, V., et al., "Constitutive Transcriptional Activation by a β-Catenin-Tcf Complex a APC${^{-/-}}$ Colon Carcinoma," *Science*, New Series, 275(5307):1784-1787, Mar. 21, 1997.

Kothary, R., et al., "A Transgene Containing *lacZ* Inserted Into the *Dystonia* Locus is Expressed in Neural Tube," *Nature 335*:435-437, Sep. 29, 1988.

Krauss, S., et al., "Expression of the Zebrafish Paired box Gene *pax[zf-b]* During Early Neurogenesis," *Development 113*:1193-1206, 1991.

Lam, K.S., "Application of Combinatorial Library Methods in Cancer Research and Drug Discovery," *Anti-Cancer Drug Des. 12*:145-167, 1997.

Lam, K.S., et al., "A new Type of Synthetic Peptide Library for Identifying Ligand-Binding Activity," *Nature 354*:82-84, Nov. 7, 1991.

Lekven, A.C., et al., "Zebrafish *wnt8* Encodes Two Wnt8 Proteins on a Bicistronic Transcript and is Required for Mesoderm and Neurectoderm Patterning," *Dev. Cell 1*:103-114, Jul. 2001.

Little, R.D., et al., "A Mutation in the LDL Receptor-Related Protein 5 Gene Results in the Autosomal Dominant High-Bone-Mass Trait," *Am. J. Hum. Genet. 70*:11-19, 2002.

Liu, J., et al., "Siah-1 Mediates a Novel β-Catenin Degradation Pathway Linking p53 to the Adenomatous Polyposis Coli Protein," *Mol. Cell 7*927-936, May 2001.

Martin, G., "Making a Vertebrate Limb: New Players Enter From the Wings," *BioEssays 23*:865-868, 2001.

Matsuzawa, S.-I., and J.C. Reed, "Siah-1, SIP, and Ebi Collaborate in a Novel Pathway for β-Catenin Degradation Linked to p53 Responses," *Mol. Cell 7*:915-926, 2001.

McMahon, A.P., and A. Bradley, "The *Wnt-1* (*int-1*) Proto-Oncogene is Required for Development of a Large Region of the Mouse Brain," *Cell 62*:1073-1085, Sep. 21, 1990.

Megason, S.G, and A.P. McMahon, "A Mitogen Gradient of Dorsal Midline Wnts Organizes Growth in the CNS," *Development 129*:2087-2098, 2002.

Moon, R.T., "Wnt/Beta-Catenin Pathway," *Science's STKE* (Connections Map, as seen in Mar. 2004), at least as early as May 2002. <<http://stke.sciencemag.org/cgi/cm/stkecm;CMP_5533>.

Moon, R.T., "*Xenopus* Egg Wnt/Beta-Catenin Pathway," *Science's STKE* (Connections Map, as seen Mar. 2004), at least as early as May 2002. <http://stke.sciencemag.org/cgi/cm/stkecm;CMP_6031>.

Moon, R.T., et al., "The Promise and Perils of Wnt Signaling Through β-Catenin," *Science 296*:1644-1646, 2002.

Müller, F., et al., "Introducing Foreign Genes into Fish Eggs With Electroporated Sperm as a Carrier," *Mol. Mar. Biol. Biotechnol. 1*(4/5):276-281, 1992.

Müller, F., et al., "Efficient Transient Expression System Based on Square Pulse Electroporation and in vivo Luciferase Assay of Fertilized Fish Eggs," *FEBS Letters 324*(1):27-32, Jun. 1993.

Murakami, Y., et al., "Micromachined Electroporation System for Transgenic Fish," *J. Biotechnol. 34*:35-42, 1994.

Novak, A., et al., "Cell Adhesion and the Integrin-Linked Kinase Regulate the LEF-1 and $\beta$-Catenin Signaling Pathways," *Proc. Natl. Acad. Sci. USA 95*(8):4374-4379, Apr. 14, 1998. <<http://links.jstor.org/sici?sici=0027-8424%2819980414%2995%3A8%3C4374%3ACAATIK%3E2.0.CO%3B2-O>.

O'Kane, C.J., and W.J. Gehring, "Detection in situ of Genomic Regulatory Elements in Drosophila," *Proc. Natl. Acad. Sci. USA 84*(24):9123-9127, Dec. 15, 1987. <<http://links.jstor.org/sici?sici=0027-8424%2819871215%2984%3A24%3C9123%3ADISOGR%3E2.0CO%3B2-O>.

Oxtoby, E., and T. Jowett, "Cloning of the Zebrafish *krox-20* Gene (*krx-20*) and its Expression During Hindbrain Development," *Nucleic Acids Res. 21*(5):1087-1095, 1993.

Pelegri, F., and H.-M. Maischein, "Function of Zebrafish β-Catenin and TCF-3 in Dorsoventral Patterning," *Mech. Dev. 77*:63-74, 1998.

Polakis, P., "Wnt Signaling and Cancer," *Genes Dev. 14*:1837-1851, 2000.

Riley, B.B., and D.J. Grunwald, "Efficient Induction of Point Mutations Allowing Recovery of Specific Locus Mutations in Zebrafish," *Proc. Natl. Acad. Sci. USA 92*:5997-6001, Jun. 1995.

Roose, J., et al., "The *Xenopus Wnt* Effector XTcf-3 Interacts With Groucho-Related Transcriptional Repressors," *Nature 395*:608-612, Oct. 8, 1998.

Ross, S.E., et al., "Inhibition of Adipogenesis by Wnt Signaling," *Science 289*:950-953, Aug. 11, 2000.

Ryu, S.-L., et al., "Regulation of *dharma/bozozok* by the Wnt Pathway," *Dev. Biol. 231*:397-409, 2001.

Schneider, S., et al., "β-Catenin Translocation Into Nuclei Demarcates the Dorsalizing Centers in Frog and Fish Embryos," *Mech. Dev. 57*:191-198, 1996.

Scott, J.K, and G.P. Smith, "Searching for Peptide Ligands With an Epitope Library," *Science*, New Series, 249(4967):386-390, Jul. 27, 1990. <<http://links.jstor.org/sici?sici=0036-8075%2819900727%293%3A249%3A4967%3C386%3AS FPLWA% 3ZE2.0.CO%3B2-9>.

Sharpe, C., et al., "Wnt Signalling: A Theme With Nuclear Variations," *BioEssays 23*:311-318, 2001.

Streisinger, G., "Attainment of Minimal Biological Variability and Measurements of Genotoxicity: Production of Homozygous Diploid ZebraFish," *Natl. Cancer Inst. Monogr. 65*, NIH Publication No. 84-2653, Bethesda, Maryland, 1984, pp. 53-58.

Symonds, J.E., et al., "Electroporation of Salmon Sperm With Plasmid DNA: Evidence of Enhanced Sperm/DNA Association," *Aquaculture 119*(11):313-327, 1994.

Szelei, J., et al., "Liposome-Mediated Gene Transfer in Fish Embryos," *Transgenic Res. 3*(2): 116-119, Mar. 1994.

Taipale, J., and P.A. Beachy, "The Hedgehog and Wnt Signalling Pathways in Cancer," *Nature 411*:349-354, May, 17, 2001.

Takada, S., et al., "*Wnt-3a* Regulates Somite and Tailbud Formation in the Mouse Embryo," *Genes Dev. 8*:174-189, Jan. 1994.

Turner, D.L., and H. Weintraub, "Expression of Achaete-Scute Homolog 3 in *Xenopus* Embryos Converts Ectodermal Cells to a Neural Fate," *Genes Dev. 8*:1434-1447, Jun. 1994.

Waterman, M.L., et al., "A Thymus-Specific Member of the HMG Protein Family Regulates the Human T Cell Receptor Cα Enhancer," *Genes Dev. 5*:656-669, Apr. 1991.

Widlund, H.R., et al., "β-Catenin-Induced Melanoma Growth Requires the Downstream Target *Microphthalmia*-Associated Transcription Factor," *J. Cell Biol. 158*:1079-1087, Nov. 6, 2002.

Wilkinson, D.G., et al., "Expression of the Proto-Oncogene *int*-1 is Restricted to Specific Neural Cells in the Developing Mouse Embryo," *Cell 50*:79-88, Jul. 3, 1987.

Wright, M., et al., "Identification of a *Wnt*-Responsive Signal Transduction Pathway in Primary Endothelial Cells," *Biochem. Biophys. Res. Commun. 263*(2):384-388, 1999.

Zelenin, A. V., et al., "The Delivery of Foreign Genes Into Fertilized Fish Eggs Using High-Velocity Microprojectiles," *FEBS Letters 287*(1/2):118-120, Aug. 1991.

Zuckermann, R.N., et al., "Discovery of Nanomolar Ligands for 7-Transmembrane G-Protein-Coupled Receptors From a Diverse *N*-(Substituted)Glycine Peptoid Library," *J. Med. Chem. 37*(17):2678-2685, 1994.

* cited by examiner

TRANSGENIC FISH AND β-CATENIN SIGNALING PATHWAY MODEL

CROSS-REFERENCE TO RELATED APPLICATION

The present application claims the benefit of U.S. Provisional Application No. 60/416,504, filed Oct. 3, 2002. This application is incorporated herein by reference.

BACKGROUND OF THE INVENTION

The present invention is directed to a Lef1/β-catenin-dependent reporter and to transgenic fish containing this reporter. The present invention is also directed to the use of the reporter and the transgenic fish as a model for the β-catenin signaling pathway. The model is useful for identifying genes in the β-catenin signaling pathway and for identifying drugs that can modulate the β-catenin signaling pathway. Such drugs are useful for treating or preventing melanoma, colorectal cancer, and osteoporosis, among other disease conditions.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Secreted Wnt ligands activate receptor-mediated signal transduction pathways, resulting in changes in gene expression, cell behavior, cell adhesion, and cell polarity. Investigations of these pathways have been driven for two decades by the knowledge that Wnt signaling is involved in both embryonic development and cancer. This knowledge has fostered a rigorous scientific dissection of Wnt signaling on the basis of genetic studies in the mouse *Mus musculus*, the fruit fly *Drosophila melanogaster*, the nematode *Caenorhabditis elegans*, and the zebrafish *Danio rerio*, as well as cell biological and biochemical studies in mammalian cultured cells and the frog *Xenopus laevis*. This worldwide effort has established that multiple Wnt signaling pathways are activated by a multigene family of Wnt ligands.

The first Wnt pathway to be discovered, and the best understood, is the canonical Wnt pathway that activates the function of β-catenin shown in FIG. 2, with more components, interactions, and target genes described in the canonical STKE Connections Map Wnt/β-catenin Pathway (Moon, 2002a). Acting through a core set of proteins that are highly conserved in evolution, this pathway regulates the ability of β-catenin to activate transcription of specific target genes. This regulation, in turn, results in changes in expression of genes that modulate cell fate, proliferation, and apoptosis. Components of the β-catenin signaling pathway are also regulated by other signals (FIG. 2), promoting interest in understanding how Wnts can function in combination with other signaling pathways. As more signaling pathways are added to the STKE Connections Maps, it will be possible for both casual users and experts to better understand and predict the outcome of increasingly complex combinatorial signaling.

Activation of the Wnt/β-catenin signaling pathway holds both promise and perils for human medicine. The perils have been known for some time—activation of this signaling pathway through loss-of-function mutations in the tumor suppressors adenomatous polyposis *coli* (APC) protein and axin, or through gain-of-function mutations in β-catenin itself, are linked to diverse human cancers, including colorectal cancers and melanomas (Polakis, 2000). This connection has fueled a search for Wnt/β-catenin pathway antagonists, which may become lead compounds for anti-cancer drugs. Greater knowledge of the Wnt/β-catenin pathway may benefit patients with other diseases and conditions, because this pathway is involved in regulating angiogenesis (Ishikawa et al., 2001; Wright et al., 1999), adipogenesis (Ross et al., 2000), and stem cell proliferation (Taipale and Beachy, 2001). For example, in the area of bone density, loss of function of a Wnt/β-catenin pathway co-receptor, low-density lipoprotein receptor-related protein 5 (LRP5), results in low bone mass in children and heterozygous parents (Gong et al., 2001). Conversely, apparent gain-of-function mutations in the same gene result in an autosomal dominant high bone-mass trait (Little et al., 2002). Thus, both antagonists and agonists of components of the Wnt/β-catenin pathway may prove therapeutic in cancer and in stimulating cell and bone replacement, respectively.

Given the clear link between the Wnt/β-catenin signaling pathway and human diseases, and the conservation of molecular functions across many animal taxa, understanding the mechanisms of Wnt signaling benefit substantially from studies in model systems. The specific pathways in the STKE Connections Maps help to promote the uses of model organisms to understand Wnt/β-catenin signaling. Currently, pathways in *Drosophila* (Boutros and Perriman, 2002), *C. elegans* (Bowerman, 2002a; Bowerman, 2002b; Bowerman, 2002c; Bowerman, 2002d) and *Xenopus* (Moon 2002b) are available, with future additions to include pathways for mouse, chicken, and zebrafish. Supporting this goal of including pathways from more species, much of the earliest work on Wnt signaling and its effects on adhesion and the cytoskeleton was conducted on mammalian cells in culture (Hinck et al., 1994), and subsequent work on the mouse has led to numerous discoveries, including the roles of Wnts as mitogens in the nervous system (Megason and McMahon, 2002), and as essential signaling factors in formation of the limbs (Martin, 2001), kidneys (Kispert et al., 1998), and female reproductive system (Heikkila et al., 2001). For a further review of Wnt pathway studies, see Moon et al. (2002).

The best characterized cellular output of Wnt/β-catenin signaling is the transcriptional activation of downstream target genes. Following Wnt pathway activation, cytoplasmic β-catenin accumulates and enters the nucleus, where it interacts with the Lef/Tcf class of transcription factors (Eastman and Grosschedl, 1999; Sharpe et al., 2001). In zebrafish, two members of this family of HMG box proteins, Lef1 and Tcf3 (Headless, Hdl), have been implicated in early development (Dorsky et al., 1999; Pelegri and Maischein, 1998; Kim et al., 2000). Lef1 has been shown to act as a β-catenin-dependent transcriptional activator through its interactions with other coactivator molecules (Billin et al., 2000). Tcf3 is a transcriptional repressor in the absence of β-catenin (Brannon et al., 1999; Roose et al., 1998). Upon β-catenin binding, Tcf3-mediated repression is relieved by an unknown mechanism. Both proteins bind to similar upstream regulatory DNA sequences, termed Lef binding sites (Waterman et al., 1991).

Analysis of a headless mutation in zebrafish has suggested that the main role of this gene during development is to repress downstream targets in the forebrain (Kim et al., 2000), in part because mutant embryos can be rescued by expression of a form of Tcf3 that does not bind β-catenin. Other potential Tcf3 targets in Xenopus, such as *siamois*, require Lef binding sites only for their repression, and not for activation (Brannon et al., 1997). The question has therefore arisen of whether Tcf3 proteins ever act as gene activators in vivo or only as repressors that can be inactivated by Wnt signaling.

Although Wnts are expressed throughout the developing embryo, the range of Wnt signaling in vivo has been difficult to determine. As a result, the cell populations and target genes that respond to Wnt/β-catenin signals during development and in disease conditions are unidentified. In order to understand the multiple roles played by Wnt/β-catenin signaling, it is important to identify these very cell populations and genes. The CNS has remained particularly unexplored with respect to Wnt targets, considering that it was the first region to be identified as expressing a vertebrate wnt gene (Wilkinson et al., 1987) and has been subsequently shown to express numerous other Wnts as well (Hollyday et al., 1995). Overexpression and loss-of-function studies have suggested roles for Wnts throughout the CNS (Dickinson et al., 1995; Ikeya et al., 1997.

Thus, it is desired to develop model systems that can be used to (a) identify genes that modulate the β-catenin signaling pathway, (b) studying the relationship between the β-catenin signaling pathway and disease conditions, such as melanoma, colorectal cancer and osteoporosis among others, and (c) screen compounds to identify drugs that can modulate the β-catenin signaling pathway.

SUMMARY OF THE INVENTION

The present invention provides new tools for determining the role the β-catenin signaling pathway plays in the physiology and pathology of the various disease conditions including, but not limited to, melanoma, colorectal cancer and osteoporosis. The tools are a Lef1/β-catenin-dependent reporter and transgenic fish, particularly transgenic zebrafish, that have integrated into their genomes a transgene encoding the Lef1/β-catenin-dependent reporter. The transgenic fish with the reporter are useful for identifying genes that modulate the β-catenin signaling pathway and for identifying cell populations with an active β-catenin signaling pathway. The transgenic fish are also useful for screening compounds to identify drugs that can modulate the β-catenin signaling pathway. These drugs will be useful for treating or preventing the described disease conditions.

Thus, in one aspect, the present invention provides a nucleic acid encoding a Lef1/β-catenin-dependent reporter. In one embodiment, the nucleic acid comprises 4 consensus Lef binding sites, a minimal promoter derived from the mouse cFos gene (Accession No. AF332140) and a reporter gene downstream of a TOPFLASH promoter and upstream of a SV40 polyadenylation site. In one aspect of this embodiment, the reporter gene is wildtype GFP. In a second aspect of this embodiment, the reporter gene is the d2GFP. A nucleic acid containing the d2GFP as the reporter gene has the map shown in FIG. 1 and the sequence shown in SEQ ID NO: 1.

In a second aspect, the present invention provides transgenic fish, particularly transgenic zebrafish (*Danio rerio*), containing the nucleic acid encoding the Lef1/β-catenin-dependent reporter in its genome.

In a third aspect, the present invention provides a method for identifying genes that modulate the β-catenin signaling pathway. Such genes that are involved in specific disease conditions are also identified according to this aspect of the invention.

In a fourth aspect, the present invention provides a method for screening compounds to identify drugs useful for treating disease conditions involving the β-catenin signaling pathway, such as melanoma, colorectal cancer and osteoporosis.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A: At dome stage (4 hpf), expression is localized to deep marginal cells on one side of the embryo, (arrowhead). FIG. 3B: By shield stage, expression is observed in the ventrolateral marginal region and in the shield hypoblast (arrowhead). FIG. 3C: At 80% epiboly, GFP expression expands throughout the ventral mesoderm (vm). FIG. 3D: Following gastrulation, mRNA is enriched at the posterior (right) end of the embryo. (Inset) Tailbud view shows exclusion of mRNA in the notochord (top). FIG. 3E: At the six-somite stage, the first expression in the nervous system is seen at the presumptive midbrain/hindbrain boundary (mhb) and hindbrain, with an obvious gap between these regions. FIG. 3F: By 18 somites, strong GFP expression is present in the midbrain region, with weaker expression in the ventral forebrain and tail mesoderm (tm). Lines indicate planes of section in FIGS. 2G-2I. FIG. 3G: Longitudinal section at 18 somites, showing expression throughout the hindbrain and medial neural crest cells (arrowheads). FIG. 3H: Transverse section through the hindbrain, with medial neural crest cells marked by arrowheads. FIG. 3I: Transverse section through the spinal cord, illustrating expression in the dorsomedial somite (som) closest to the neural tube, and in an intermediate zone of the CNS.

FIG. 5A: Following injection with DNA encoding Wnt1-myc, ectopic reporter expression is induced outside the endogenous domain of GFP (arrowhead). (Inset) This cell expresses both Wnt1-myc, as detected by anti-myc immunostaining (red), and GFP (green). In all following panels, red autofluorescence is shown for contrast. FIG. 5B: Twelve-somite embryo. mhb, midbrain/hindbrain boundary. Box indicates region depicted at higher power in FIG. 5C. FIG. 5C: GFP is strongly expressed in the tail epiblast and hypoblast (arrowhead) and presomitic mesoderm (psm). FIG. 5D: 24-hpf embryo. Box indicates region depicted at higher power in FIG. 5E. FIG. 5E: GFP is present at low levels in the brain and higher levels in the otic vesicle (ov), migrating pigment cells (arrowhead), and posterior lateral line ganglion (pllg). FIG. 5F: 48-hpf embryo. Left box indicates region depicted in FIG. 5G and right box indicates region depicted in FIG. 5H. FIG. 5G: While expression decreases in the otic vesicle (ov), it is maintained at a high level in the posterior lateral line ganglion (pllg). FIG. 5H: High-power view of the posterior spinal cord shows specific TOPdGFP expression in individual neurons. FIG. 5I: 72-hpf embryo. GFP is expressed in the dorsal midbrain, lens, and cranial ganglia (arrowheads).

(FIGS. 6A-6C) 24 hpf; (FIGS. 6D-6F) 36 hpf; (FIGS. 6G-6I) 48 hpf. FIG. 6A: Midbrain rostral to the eye is shown. FIG. 6B: Section through caudal eye region. rpe, retinal pigmented epithelium. FIG. 6C: Spinal cord section, showing individual GFP-labeled neurons. FIG. 6D: Eye and midbrain region. Eyes are outlined in white dotted lines, lens is indicated by arrowhead. FIG. 6E: Hindbrain section. Individual neurons in the ventral hindbrain express GFP. FIG. 6F: In the spinal cord, expression is seen at multiple dorsal/ventral positions and in dorsal pigment cells (arrowheads). Pigment cells are identifiable by their morphology and position just below the ectoderm. FIG. 6G: Extensive GFP expression is present in the dorsal midbrain. FIG. 6H: Section just caudal to ear. pllg, posterior lateral line ganglion. FIG. 6I: Spinal cord expression is similar to domains observed at 36 hpf.

DETAILED DESCRIPTION OF THE PREFERRED EMBODIMENT

To examine the targets of Wnt/β-catenin signaling, an in vivo reporter system has been created that can identify β-catenin-responsive cells and genes. The TOPFLASH reporter has been extensively used to quantitate β-catenin-dependent transcription (Korinek et al., 1997), by expression of luciferase under the control of multiple Lef binding sites and a basal cFos promoter. In one embodiment, by employing a destabilized GFP, a transient reporter (TOPdGFP) has been created that is visible in living tissue with fluorescence optics. In a second embodiment, a wildtype GFP or any other suitable reporter molecule can be used in place of the destablized GFP. Zebrafish is used as the transgenic organism, taking advantage of its optical clarity and rapid development to enable live imaging of reporter activity. A further advantage of zebrafish is its accessibility to both embryonic and genetic manipulations, vastly expanding the array of functional studies that can be undertaken with this system.

Figure 1:
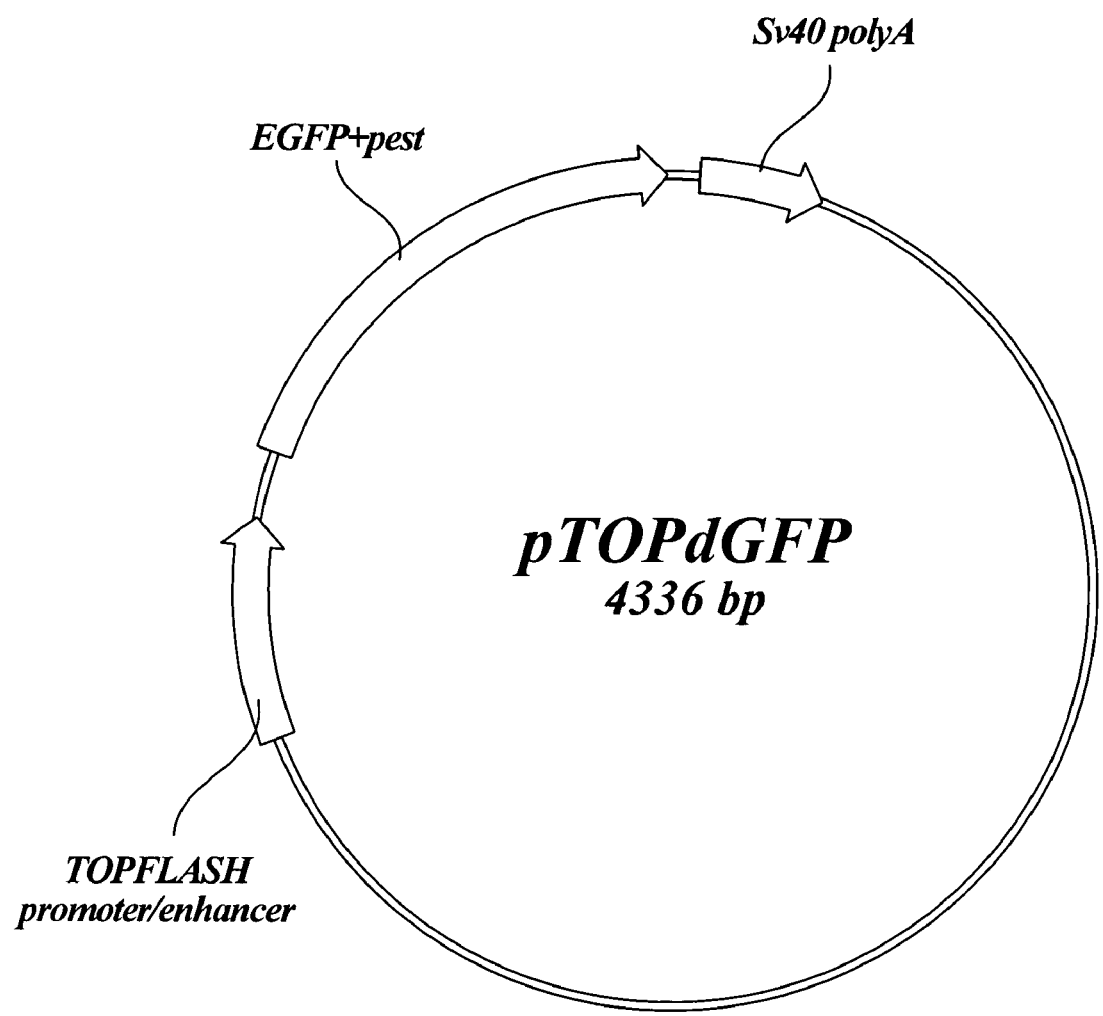
FIG. 1 shows the map of the plasmid TOPdGFP. The nucleic acid sequence of this plasmid is set forth in SEQ ID NO: 1. The nucleotide positions are defined from the first nucleotide in the sequence which is +1. The SV40 polyA is at nucleotides 38-243. The TOPFLASH enhancer is at nucleotides 3005-3374. The EGFP+pest is at nucleotides 3485-4327. The plasmid also includes an ampicilin resistance selectable marker.
Figure 2:
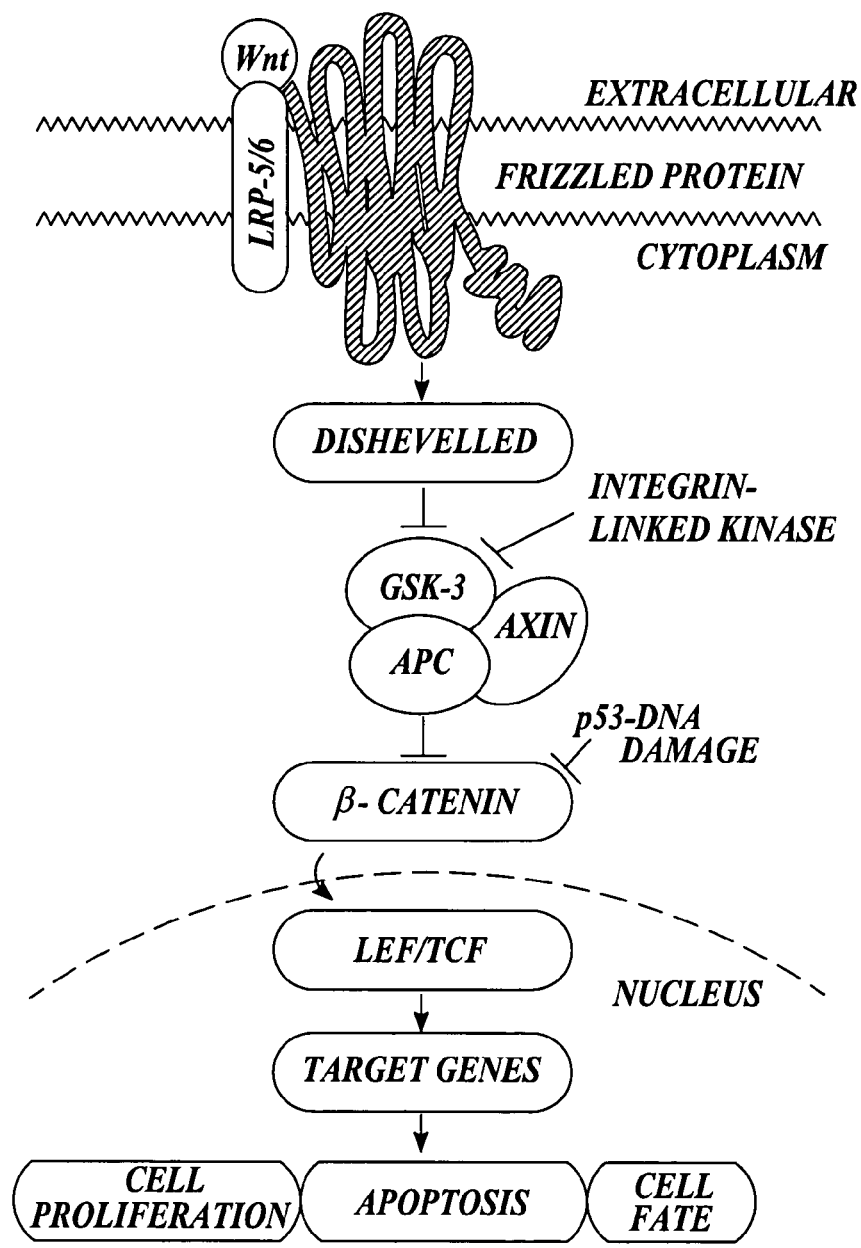
FIG. 2 shows core elements of the Wnt/β-catenin pathway, depicting how activation of the Frizzled receptor by the Wnt ligand leads to activation of the function of β-catenin. This activation, in turn, activates gene expression leading to diverse cellular responses in both embryonic development and in adults. Other pathways, such as integrin-linked kinase and p53, also regulate β-catenin.

The transient reporter (TOPdGFP) as present in a plasmid vector is shown in FIG. 1 and the nucleotide sequence is set forth in SEQ ID NO: 1. Thus, one aspect of the present invention is an isolated nucleic acid that comprises a DNA molecule which functions as a reporter molecule. In a first embodiment, the DNA molecule comprises nucleotides 3005-4336 of SEQ ID NO:1 contiguous to nucleotides 1-243 of SEQ ID NO:1 In a second embodiment, the DNA molecule comprises a nucleotide sequence having at least 80% identity, preferably at least 90% identity, more preferably, at least 95% identity and most preferably at least 98% identity, with this sequence and which has the same reporter function. A second aspect of the present invention is this nucleic acid contained within a vector. One such vector is shown in FIG. 1.

In a third embodiment, a wildtype GFP is used in place of the destablized GFP. The vector shown in FIG. 1 can be modified by substituting the wildtype GFP gene sequence, such as set forth in Genbank Accession No. M62653 for the nucleic acid sequence of destabilized GFP. The destabilized GFP sequence includes nucleotides 3485-4330 of SEQ ID NO:1 which can be substituted by a coding sequence for wildtype GFP. A nucleic acid sequence encoding a wildtype GFP is shown in SEQ ID NO:2. In a fourth embodiment, the DNA molecule comprises a nucleotide sequence having at least 80% identity, preferably at least 90% identity, more preferably, at least 95% identity and most preferably at least 98% identity, with this sequence and which has the same reporter function.

Many additional reporter proteins are known and have been used for similar purposes. These include enzymes, such as β-galactosidase, luciferase, and alkaline phosphatase, that can produce specific detectable products, and proteins that can be directly detected. Virtually any protein can be directly detected by using, for example, specific antibodies to the protein. Any reporter which can be readily detected may be used in place of the destabilized or wildtype GFP.

A nucleic acid or fragment thereof has substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, more preferably at least about 95% of the nucleotide bases, and more preferably at least about 98% of the nucleotide bases. A protein or fragment thereof has substantial identity with another if, optimally aligned, there is an amino acid sequence identity of at least about 30% identity with an entire naturally-occurring protein or a portion thereof, usually at least about 70% identity, more usually at least about 80% identity, preferably at least about 90% identity, more preferably at least about 95% identity, and most preferably at least about 98% identity.

Identity means the degree of sequence relatedness between two polypeptides or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D., *SIAM J Applied Math*. 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12(1).387 (1984)), BLASTP, BLASTN, FASTA (Altschul et al. (1990); Altschul et al. (1997)). The well-known Smith Waterman algorithm may also be used to determine identity.

As an illustration, by a polynucleotide having a nucleotide sequence having at least, for example, 95% "identity" to a reference nucleotide sequence of is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Asubel, 1992; Wetmur and Davidson, 1968.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 µg/ml denatured, sheared salmon sperm DNA, followed by washing the filters in 0.1×SSC at about 65° C.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% w/w of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

Transgenic fish, particularly zebrafish, carrying the transient reporter, TOPdGFP, or other reporter molecules disclosed herein, including wildtype GFP, are produced in accordance with the present invention. The transgenic zebrafish are useful for identifying genes that modulate the β-catenin signaling pathway and for identifying drugs that modulate the β-catenin signaling pathway.

The present invention relates to a method of determining the ability of a test agent or compound to modulate the β-catenin signaling pathway. A preferred method comprises administering the test agent to a transgenic fish which is expressing a Lef1/β-catenin-dependent reporter and then assaying for changes in β-catenin signaling pathway function. Such method is useful for identifying compounds which are able to ameliorate the symptoms that result from the involvement of the β-catenin signaling pathway and assessing the efficacy of the test compound on pathological symptoms that are associated with β-catenin signaling pathway.

Disclosed are transgenic fish, and a method of making transgenic fish, which express a Lef1/β-catenin-dependent reporter in stable and predictable tissue- or developmentally-specific patterns. Also disclosed are methods of using such transgenic fish. Such expression of the reporter allow the study of developmental processes, the relationship of cell lineages, the assessment of the effect of specific genes and compounds on the development or maintenance of specific tissues or cell lineages, and the maintenance of lines of fish bearing mutant genes. The disclosed transgenic fish are characterized by homologous expression sequences in an exogenous construct introduced into the fish or a progenitor of the fish.

As used herein, transgenic fish refers to fish, or progeny of a fish, into which an exogenous construct has been introduced. A fish into which a construct has been introduced includes fish which have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded. However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

The examples illustrate the manner in which transgenic fish exhibiting the Lef1/β-catenin-dependent reporter can be made and used. The transgenic fish described in the examples, and the transgene constructs used, are particularly useful for detection of fish expressing the transgene, the identification of genes that modulate the β-catenin signaling pathway and the identification of drugs that modulate the β-catenin signaling pathway.

Transgene constructs are the genetic material that is introduced into fish to produce a transgenic fish. Such constructs are artificially introduced into fish. The manner of introduction, and, often, the structure of a transgene construct, render such a transgene construct an exogenous construct. Although a transgene construct can be made up of any nucleic acid sequences, for use in the disclosed transgenic fish it is preferred that the transgene constructs combine expression sequences operably linked to a sequence encoding an expression product. The transgenic construct will also preferably include other components that aid expression, stability or integration of the construct into the genome of a fish. As used herein, components of a transgene construct referred to as being operably linked or operatively linked refer to components being so connected as to allow them to function together for their intended purpose. For example, a promoter and a coding region are operably linked if the promoter can function to result in transcription of the coding region.

Expression sequences are used in the disclosed transgene constructs to mediate expression of an expression product encoded by the construct. As used herein, expression sequences include promoters, upstream elements, enhancers, and response elements. It is preferred that the expression sequences used in the disclosed constructs be homologous expression sequences. As used herein, in reference to components of transgene constructs used in the disclosed transgenic fish, homologous indicates that the component is native to or derived from the species or type of fish involved. Conversely, heterologous indicates that the component is neither native to nor derived from the species or type of fish involved.

As used herein, expression sequences are divided into two main classes, promoters and enhancers. A promoter is generally a sequence or sequences of DNA that function when in a relatively fixed location in regard to the transcription start site. A promoter contains core elements required for basic interaction of RNA polymerase and transcription factors, and may contain upstream elements and response elements. Enhancer generally refers to a sequence of DNA that functions at no fixed distance from the transcription start site and can be in either orientation. Enhancers function to increase transcription from nearby promoters. Enhancers also often contain response elements that mediate the regulation of transcription. Promoters can also contain response elements that mediate the regulation of transcription.

Enhancers often determine the regulation of expression of a gene. This effect has been seen in so-called enhancer trap constructs where introduction of a construct containing a reporter gene operably linked to a promoter is expressed only when the construct inserts into the domain of an enhancer (O'Kane and Gehring, 1987; Allen et al., 1988; Kothary et al., 1988; Gossler et al., 1989). In such cases, the expression of the construct is regulated according to the pattern of the newly associated enhancer. Transgenic constructs having only a minimal promoter can be used in the disclosed transgenic fish to identify enhancers.

For expression of encoded peptides or proteins, a transgene construct also needs sequences that, when transcribed into RNA, mediate translation of the encoded expression products. Such sequences are generally found in the 5' untranslated region of transcribed RNA. This region corresponds to the region on the construct between the transcription initiation site and the translation initiation site (that is, the initiation codon). The 5' untranslated region of a construct can be derived from the 5' untranslated region normally associated with the promoter used in the construct, the 5' untranslated region normally associated with the sequence encoding the expression product, the 5' untranslated region of a gene unrelated to the promoter or sequence encoding the expression product, or a hybrid of these 5' untranslated regions. Preferably, the 5' untranslated region is homologous to the fish into which the construct is to be introduced. Preferred 5' untranslated regions are those normally associated with the promoter used.

Transgene constructs for use in the disclosed transgenic fish encode a reporter protein (for detection and quantitation of expression). As used herein, a reporter protein is any protein that can be specifically detected when expressed.

Reporter proteins are useful for detecting or quantitating expression from expression sequences. For example, operatively linking nucleotide sequence encoding a reporter protein to a tissue specific expression sequences allows one to carefully study lineage development. In such studies, the reporter protein serves as a marker for monitoring developmental processes, such as cell migration. Many reporter proteins are known and have been used for similar purposes in other organisms. These include enzymes, such as β-galactosidase, luciferase, and alkaline phosphatase, that can produce specific detectable products, and proteins that can be directly detected. Virtually any protein can be directly detected by using, for example, specific antibodies to the protein. In accordance with the preferred embodiment of the present invention, the reporter protein is a destabilized green fluorescent protein (GFP).

The use of reporter proteins that, like GFP, are directly detectable without requiring the addition of exogenous factors are preferred for detecting or assessing gene expression during zebrafish embryonic development. A transgenic zebrafish embryo, carrying a construct encoding a reporter protein and a tissue-specific expression sequences, can provide a rapid real time in vivo system for analyzing spatial and temporal expression patterns of developmentally regulated genes.

The disclosed transgene constructs preferably include other sequences which improve expression from, or stability of, the construct. For example, including a polyadenylation signal on the constructs encoding a protein ensures that transcripts from the transgene will be processed and transported as RNA. The identification and use of polyadenylation signals in expression constructs is well established. It is preferred that homologous polyadenylation signals be used in the transgene constructs.

The disclosed constructs are preferably integrated into the genome of the fish. However, the disclosed transgene construct can also be constructed as an artificial chromosome. Such artificial chromosomes containing more that 200 kb have been used in several organisms. Artificial chromosomes can be used to introduce very large transgene constructs into fish. This technology is useful since it can allow faithful recapitulation of the expression pattern of genes that have regulatory elements that lie many kilobases from coding sequences.

The disclosed constructs and methods can be used with any type of fish. As used herein, fish refers to any member of the classes collectively referred to as pisces. It is preferred that fish belonging to species and varieties of fish of commercial or scientific interest be used. Such fish include salmon, trout, tuna, halibut, catfish, zebrafish, medaka, carp, tilapia, goldfish, and loach.

The most preferred fish for use with the disclosed constructs and methods is zebrafish, *Danio rerio*. Zebrafish are an increasingly popular experimental animal since they have many of the advantages of popular invertebrate experimental organisms, and include the additional advantage that they are vertebrates. Another significant advantage of zebrafish is that, like *Caenorhabditis*, they are largely transparent (Kimmel, 1989). The generation of thousands of zebrafish mutants (Driever et al., 1996); Haffter et al., 1996) provides abundant raw material for transgenic study of these animals. General zebrafish care and maintenance is described by Streisinger, 1984).

Zebrafish embryos are easily accessible and nearly transparent. Given these characteristics, a transgenic zebrafish embryo, carrying a construct encoding a reporter protein and tissue-specific expression sequences, can provide a rapid real time in vivo system for analyzing spatial and temporal expression patterns of developmentally regulated genes. In addition, embryonic development of the zebrafish is extremely rapid. In 24 hours an embryo develops rudiments of all the major organs, including a functional heart and circulating blood cells (Kimmel, 1989). Other fish with some or all of the same desirable characteristics are also preferred.

The disclosed transgenic fish are produced by introducing a transgene construct into cells of a fish, preferably embryonic cells, and most preferably in a single cell embryo. Where the transgene construct is introduced into embryonic cells, the transgenic fish is obtained by allowing the embryonic cell or cells to develop into a fish. Introduction of constructs into embryonic cells of fish, and subsequent development of the fish, are simplified by the fact that embryos develop outside of the parent fish in most fish species.

The disclosed transgene constructs can be introduced into embryonic fish cells using any suitable technique. Many techniques for such introduction of exogenous genetic material have been demonstrated in fish and other animals. These include microinjection (described by, for example, Culp et al., 1991), electroporation (described by, for example, Inoue et al., 1990; Muller et al., 1993; Murakami et al., 1994; Muller et al., 1992; Symonds et al., 1994), particle gun bombardment (Zelenin et al., 1991), and the use of liposomes (Szelei et al., 1994). Microinjection is preferred. The preferred method for introduction of transgene constructs into fish embryonic cells by microinjection is described in the examples.

Embryos or embryonic cells can generally be obtained by collecting eggs immediately after they are laid. Depending on the type of fish, it is generally preferred that the eggs be fertilized prior to or at the time of collection. This is preferably accomplished by placing a male and female fish together in a tank that allows egg collection under conditions that stimulate mating. After collecting eggs, it is preferred that the embryo be exposed for introduction of genetic material by removing the chorion. This can be done manually or, preferably, by using a protease such as pronase. A preferred technique for collecting zebrafish eggs and preparing them for microinjection is described in the examples. A fertilized egg cell prior to the first cell division is considered a one cell embryo, and the fertilized egg cell is thus considered an embryonic cell.

After introduction of the transgene construct the embryo is allowed to develop into a fish. This generally need involve no more than incubating the embryos under the same conditions used for incubation of eggs. However, the embryonic cells can also be incubated briefly in an isotonic buffer. If appropriate, expression of an introduced transgene construct can be observed during development of the embryo.

Fish harboring a transgene can be identified by any suitable means. For example, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct is preferably accomplished by Southern or Northern blotting. Also preferred is detection using polymerase chain reaction (PCR) or other sequence-specific nucleic acid amplification techniques. Preferred techniques for identifying transgenic zebrafish are described in the examples.

Identifying the pattern of expression in the disclosed transgenic fish can be accomplished by measuring or identifying expression of the transgene in different tissues (tissue-specific expression), at different times during development (developmentally regulated expression or developmental stage-specific expression), in different cell lineages (cell lineage-specific expression). These assessments can also be combined by, for example, measuring expression (and observing changes, if any) in a cell lineage during development. The nature of the expression product to be detected can have an effect on the suitability of some of these analyses. On one level, different tissues of a fish can be dissected and expression can be assayed in the separate tissue samples. Such an assessment can be performed when using almost any expression product. This technique is commonly used in transgenic animals and is useful for assessing tissue-specific expression.

This technique can also be used to assess expression during the course of development by assaying for the expression product at different developmental stages. Where detection of the expression product requires fixing of the sample or other treatments that destroy or kill the developing embryo or fish, multiple embryos must be used. This is only practical where the expression pattern in different embryos is expected to be the same or similar. This will be the case when using the disclosed transgenic fish having stable and predictable expression.

A more preferred way of assessing the pattern of expression of a transgene during development is to use an expression product that can be detected in living embryos and animals. A preferred expression product for this purpose is the green fluorescent protein. A preferred form of GFP and a preferred technique for measuring the presence of GFP in living fish is described in the examples.

In zebrafish, the nervous system and other organ rudiments appear within 24 hours of fertilization. Since the nearly transparent zebrafish embryo develops outside its mother, the origin and migration of lineage progenitor cells can be monitored by following expression of an expression product in transgenic fish. In addition, the regulation of a specific gene can be studied in these fish.

Transgenic fish expressing the TOPdGFP reporter gene are useful for the identification of genes that modulate the β-catenin signaling pathway. Fish expressing the TOPdGFP reporter can be mated with fish raised from embryos that have been treated with a chemical mutagen (see for example: Imai et al., 2000; Hafter et al., 1996; Driever et al., 1996; Riley and Grunwald, 1996) or with an insertional retrovirus (see for example: Golling et al., 2002; Burgess and Hopkins, 2000; Amsterdam and Hopkins, 1999). Alterations in the levels of the reporter gene product in progeny fish assessed, for example, by fluorescence measurements may represent the inaction or over-expression of a gene(s) whose function has become altered by the presence of a chemically-derived or retrovirally-derived mutation.

It is also possible to detect genes that modulate the β-catenin signaling pathway by fertilizing eggs derived from fish expressing the TOPdGFP reporter gene with sperm derived from a library of fish bearing retroviral insertions. Alterations in the levels of the reporter gene product in progeny may represent the inaction or over-expression of a gene(s) whose function has become altered by the presence of a retroviral insertion. The nature of the retrovirus-altered gene can be determined by detection of the retroviral insertion which acts as a molecular tag of that gene.

The disclosed transgenic fish can be exposed to compounds to assess the effect of the compound on the modulation of the β-catenin signaling pathway. For example, test compounds can be administered to transgenic fish harboring an exogenous construct containing the expression sequence of a reporter protein. By comparing the expression of the reporter protein in fish exposed to a test compound to those that are not exposed, the effect of the compound on the modulation of the β-catenin signaling pathway can be assessed. Test compounds can act as either inhibitors or activators of the reporter gene. In this manner, compounds which are useful as drugs for treating or preventing disease conditions associated with β-catenin signaling pathway, such as melanoma, colorectal cancer and osteoporosis, are identified.

The activity of β-catenin is regulated positively by signaling molecules of the Wnt family and negatively by molecules such as glkycogen synthase kinase (GSK3β) and adenomatous polyposis coli protein (APC). Compounds that modulate these actions may affect the activity of β-catenin and thus may have similar utility as drugs for treating or preventing disease conditions associated with β-catenin signaling pathway. Additionally, β-catenin exerts a positive influence on Microphthalmia-associated transcription factor (MITF) which is known to modulate melanocyte differentiation and pigmentation (Widlund et al., 2002). The action of β-catenin on MITF is required as a potent mediator of growth for melanoma cells. Thus compounds that interfere with or alter the interaction between β-catenin and MITF may have utility in the treatment of melanoma.

A variety of test compounds can be evaluated in accordance with the present invention. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al., 1992; DeWitt et al., 1993), peptoids (Zuckermann, 1994), oligocarbamates (Cho et al., 1993), and hydantoins (DeWitt et al., 1993). An approach for the synthesis of molecular libraries of small organic molecules with a diversity of 104-105 as been described (Carell et al., 1994a; Carell et al., 1994b).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, 1997). Other exemplary methods for the synthesis of molecular libraries can be found in the art, for example in: Erb et al. (1994); Horwell et al (1996); Gallop et al. (1994).

Libraries of compounds may be presented in solution (e.g., Houghten, 1992), or on beads (Lam, 1991), chips (Fodor, 1993), bacteria (U.S. Pat. No. 5,223,409), spores (U.S. Pat. No. 5,223,409), plasmids (Cull et al., 1992) or on phage (Scott and Smith, 1990; Devlin, 1990; Cwirla et al., 1990; Felici, 1991). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel etal., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th ed., Univ. of Oregon Press, Eugene, 2000).

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Generation of TOPdGFP: A 358-bp promoter/enhancer region of TOPFLASH (Korinek et al., 1997), containing 4 consensus Lef binding sites and a minimal promoter, was amplified by PCR. The 94-bp minimal promoter is derived from the mouse cFos gene (Accession No. AF332140), starting 38 bp 5' to the TATA box, and has no activity in zebrafish on its own. This fragment was inserted into the vector pCS2+ (Turner and Weintraub, 1994), replacing the CMV promoter. The d2GFP gene (Clontech, Palo Alto, Calif.) was then inserted into this construct downstream of the TOP promoter and upstream of the SV40 polyadenylation site.

DNA Injections and Production of Transgenic Fish: Approximately 100 pg of TOPdGFP DNA was injected into a one-cell wild-type zebrafish embryo, into the yolk just below the blastoderm. Injections of 100-150 embryos were performed on multiple days. After 6 h, embryos were screened for GFP expression and positive embryos were sorted and raised to adulthood.

Adult fish were intercrossed and at least 100 embryos per pair were screened at 24 h postfertilization (hpf) by fluorescence microscopy for GFP expression. Because more male than female fish were generated, some males were screened by crossing to wild-type females. Out of 152 adult fish screened, one founder male that produced 10% transgenic progeny was identified. Heterozygous $F_1$ embryos were raised to adulthood to establish a line and inter-crossed to generate homozygous progeny. This transgenic line has been given the allele designation TG(TOP:dGFP)w25. GFP imaging was performed by using a Nikon PCM2000 confocal microscope and images were processed with Adobe Photoshop 5.0.

For Wnt1 overexpression experiments, transgenic embryos were injected at the one-cell stage with 100 pg of pCS2+wnt1-myc DNA. Injected embryos were fixed at 18 hpf, then processed for anti-myc immunostaining using a Cy3-labeled secondary antibody.

In Situ Hybridizations: In situ hybridization was performed as described previously (Oxtoby and Jowett, 1993). The GFP probe was made by antisense transcription of TOPdGFP, using a T7 promoter present in the construct. The Probe for hdl was made from a full-length clone isolated in our laboratory, subcloned into pCS2+. Probes for pax2.1 (Krauss et al., 1991), tbx6 (Hug et al., 1997), and lef1 (Dorsky et al., 1999) were made as described previously. Images were taken with a Kodak DC290 digital camera and processed with Adobe Photoshop 5.0.

Morpholino Injections: Morpholino antisense oligonucleotides targeted to lef1 and hdl were obtained from Gene Tools (Corvallis, Oreg.). lef1 MO sequence: 5'- CTCCTC-CACCTGACAACTGCGGCAT-3' (SE ID NO:3); hdl MO sequence: 5'- CTCCGTTTAACTGAGGCATGTTGGC-3 (SEQ ID NO:4).

Approximately 1 ng of the morpholinos was injected into one-cell homozygous transgenic embryos that were fixed for in situ hybrid-ization at appropriate stages. Injections of control morpholinos produced no effect on TOPdGFP expression.

Sections: Fixed embryos were rinsed in phosphate-buffered saline, equilibrated in 30% sucrose, embedded in Tissue-Tek OCT mounting medium, and frozen on dry ice. Sections (12 mM) were cut on a Reichert-Jung cryostat, rinsed, and coverslipped in Vectashield mounting medium.

Example 2

Generation of TOPdGFP Transgenic Zebrafish

The TOPdGFP reporter construct contains four consensus Lef binding sites and a minimal cFos promoter, driving a destabilized GFP transgene. This reporter should only be transcriptionally active in the presence of both stabilized β-catenin and Lef/Tcf proteins. When the TOPdGFP construct is injected into one-cell zebrafish embryos to test expression, GFP fluorescence is observed from approximately 6 hpf continuing throughout development. Expression was mosaic, and variations between individual embryos were apparent. Removal of the Lef binding sites resulted in no reporter expression in any injected embryo. We therefore concluded that the TOP-dGFP construct was active in zebrafish and raised injected fish to adulthood.

After adult fish were screened by intercrossing or by outcrossing to a wild-type line, a mosaic founder fish that produced 10% transgenic embryos was recovered. In preliminary surveys, these embryos expressed GFP at high levels in the midbrain when observed under a fluorescence dissecting microscope. GFP fluorescence is not observed before 12 hpf using confocal microscopy. This could be due to several factors, including low expression levels at early stages of development and positional effects of local genomic DNA. Confirming turnover of the destabilized GFP protein, many areas of expression visible at 12-16 hpf, such as presomitic mesoderm, were not visibly fluorescent 24 h later.

Example 3

Early Expression of TOPdGFP Mirrors Known Domains of Wnt/β-Catenin Signaling

Figure 3A:
FIGS. 3A-3I show that TOPdGFP expression reflects known domains of Wnt/b-catenin signaling. Animal pole views are shown in FIG. 3A and FIG. 3B. Lateral views are shown in FIGS. 2C-2F, with ventral to the left in FIG. 3C and anterior to the left in FIGS. 3D-3F.
Figure 3B:
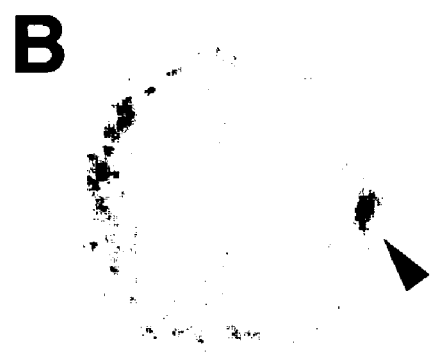
Figure 3C:
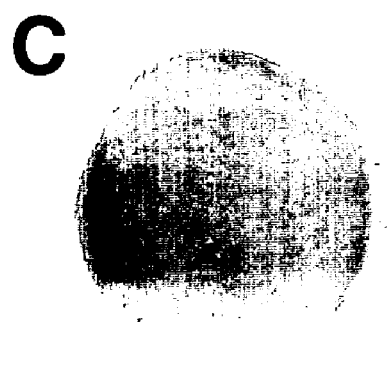
Figure 3D:
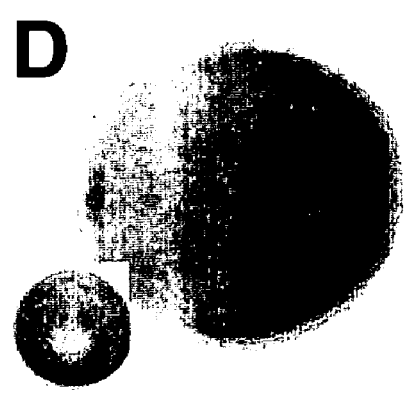
Figure 3E:
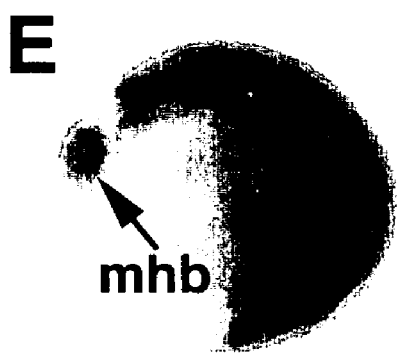
Figure 3F:
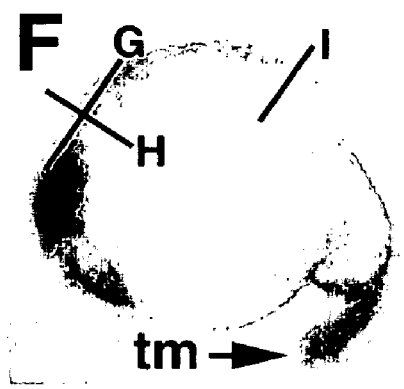

To examine whether TOPdGFP is expressed earlier in development than was evident by GFP fluorescence, in situ hybridization was performed on transgenic embryos at stages following the onset of zygotic transcription. Using this more sensitive technique, TOPdGFP expression is observed in known domains of Wnt signaling, consistent with its being a faithful reporter of this pathway. At 4 hpf, the first expression is observed in a small group of cells at the embryonic margin (FIG. 3A). Although it is impossible to morphologically determine the future dorsal axis in zebrafish embryos at this stage, this expression is consistent with the site of nuclear β-catenin accumulation (Schneider et al., 1996) and the expression of β-catenin target genes such as squint and bozozok (Kelly et al., 2000; Ryu et al., 2001). During gastrulation, localized expression was observed in the embryonic shield (FIG. 3B), supporting the assumption that the pregastrulation expression is dorsal. At shield stage, expression is observed in the ventrolateral mesoderm (FIG. 3B), the site of the first known zygotic Wnt activity, produced by Wnt8 (Christian et al., 1991). This expression expands during gastrulation, covering most of the ventral mesoderm by 80% epiboly (vm; FIG. 3C). By bud stage, all mesoderm in the posterior embryo expresses TOPdGFP, with the exception of the notochord (FIG. 3D). The first observable expression in the neurectoderm was at 12 hpf, when GFP mRNA is detected in the midbrain-hindbrain boundary (mhb), hind-brain, and spinal cord (FIG. 3E). Both neurectoderm and tail mesoderm expression continued until 18 hpf (FIG. 3F), the latest stage we examined with this technique. In summary, at least four known domains requiring Wnt/β-catenin signaling are reported by TOPdGFP: the dorsal organizer (maternal β-catenin; Heasman et al., 1994; Schneider et al., 1996; Kelly et al., 2000), ventrolateral mesoderm (Wnt8; Lekven et al., 2001), tailbud (Wnt3a; Takada et al., 1994), and mhb (Wnt1; McMahon and Bradley, 1990).

Figure 3G:
Figure 3H:
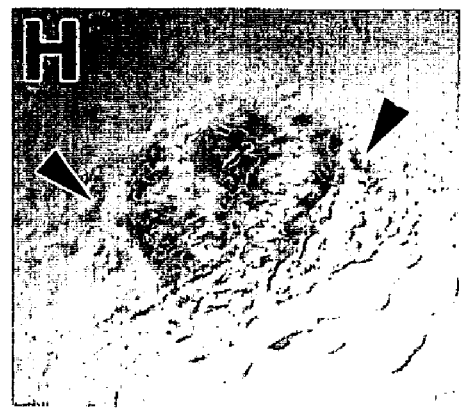
Figure 3I:
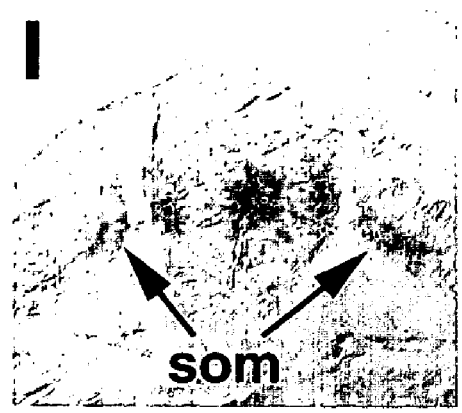

In order to investigate early TOPdGFP expression in more detail, 18-hpf embryos were sectioned-stained by in situ hybridization. Through this analysis, transgene expression is observed in medial neural crest (FIGS. 3G and 3H), supporting earlier findings that Wnt signaling plays a role in neural crest fate specification (Dorsky et al., 1998; Dorsky et al., 2000). Sections through more caudal regions of the embryo showed additional domains of expression including presumptive commissural interneuron progenitors (Bernhardt et al., 1990), and the medial lip of developing somites (FIG. 3I).

Example 4

Lef1, but not Tcf3, Regulates Reporter Expression in vivo

Although the above observations provided circumstantial evidence that TOPdGFP reports endogenous Wnt signaling, it was possible that transgene expression in known Wnt-responsive domains was coincidental. However, it is apparent that TOPdGFP expression bears a resemblance to zygotic expression of lef1 (compare FIG. 3 to FIGS. 4B, 4D, and 4F). In contrast, TOPdGFP appears to be expressed in a complimentary pattern to hdl (Compare FIG. 3 to FIGS. 4A, 4C, and 4E). Since lef1 has been shown to mediate Wnt-dependent gene activation while hdl functions primarily as a repressor, the hypothesis that the activity of either gene is required for reporter expression was tested. To partially inhibit gene function, morpholino antisense oligonucleotides targeted against zebrafish hdl and lef1 were injected. Both morpholinos can specifically block translation of the respective expression plasmids in reticulocyte lysates.

Figure 4A:
FIGS. 4A-4U show that reporter expression requires lef1, but not hdl, activity. Animal pole views are shown in FIG. 4A and FIG. 4B. Anterior views with dorsal to the right are shown in FIGS. 4C, 4D, 4H, 4J, 4M, 4O, 4R, 4T. Posterior views with dorsal to the left are shown in FIGS. 4E, 4F, 4I, 4K, 4N, 4P, 4S, 4U). Arrowheads mark the rostral limit of the neurectoderm. At shield stage, hdl is expressed throughout the epiblast (FIG. 4A), while lef1 is expressed primarily in the germ ring (FIG. 4B), similar to TOPdGFP (compare to FIG. 3B). At bud stage, hdl is expressed in the anterior neurectoderm and underlying prechordal plate (FIG. 4C), while lef1 expression is absent in this region (FIG. 4D), similar to TOPdGFP (compare to FIG. 4T). hdl is expressed very weakly in the tailbud (tb) at bud stage (FIG. 4E), while lef1 is expressed at high levels in this region (FIG. 4F), similar to TOPdGFP (compare to FIG. 4U). Injection of a hdl morpholino phenocopies the hdl mutant at 36 hpf, causing loss of telencephalon and eyes (FIG. 4G). The hdl morpholino results in rostral expansion of pax2 (compare FIG. 4H and FIG. 4R), but has no effect on tbx6 expression (compare FIG. 4I and FIG. 4S). Loss of hdl has no effect on expression of TOPdGFP in the anterior neurectoderm (compare FIG. 4J and FIG. 4T) or in the tailbud (compare FIG. 4K and FIG. 4U). Injection of a lef1 morpholino results in loss of tail structures posterior to the yolk extension at 36 hpf (FIG. 4L). While the lef1 morpholino has no effect on pax2 expression (compare FIG. 4M and FIG. 4R), it significantly decreases tbx6 (compare FIG. 4N and FIG. 4S). Similarly, loss of lef1 has no effect on anterior TOPdGFP expression (compare FIG. 4O and FIG. 4T), but it significantly decreases expression in the tailbud (compare FIG. 4P and FIG. 4U).
Figure 4B:
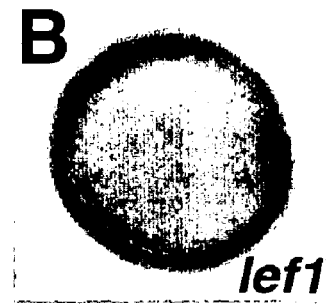
Figure 4C:
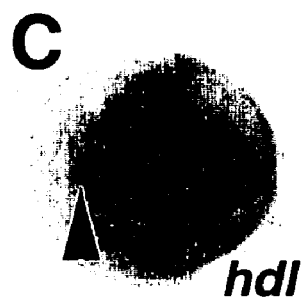
Figure 4D:
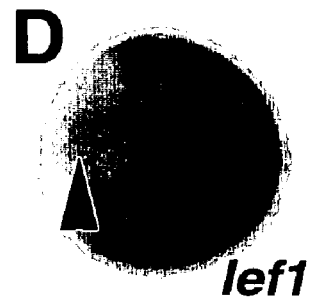
Figure 4E:
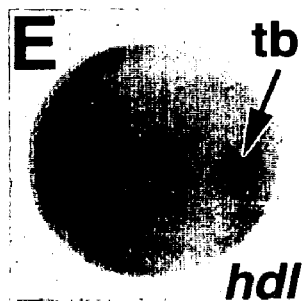
Figure 4F:
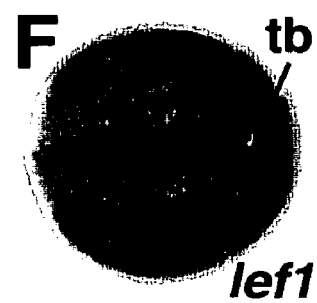
Figure 4G:
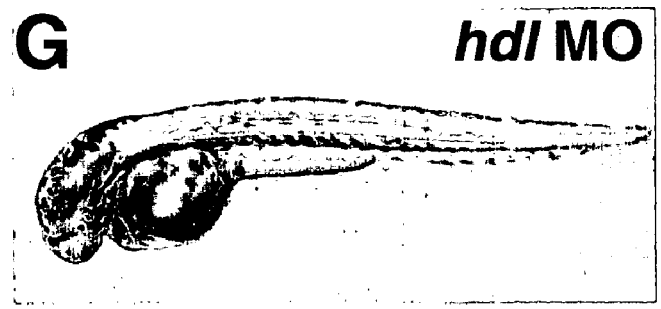
Figure 4H:
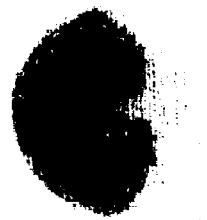
Figure 4I:
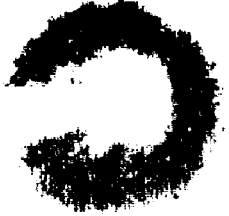
Figure 4J:
Figure 4K:

The function of hdl as a repressor of posterior neural gene expression led to test of whether the inhibition of hdl would expand TOPdGFP expression in transgenic embryos. Injection of the hdl morpholino at the one-cell stage results in a phenotype indistinguishable from hdl mutant embryos at 36 hpf (FIG. 4G). At bud stage, loss of hdl function results in the anterior expansion of midbrain markers such as pax2 (FIG. 4H), but has no effect on the expression of ventrolateral mesoderm markers such as spt (not shown) and tbx6 (FIG. 4I). Interestingly, the hdl morpholino does not expand anterior TOPdGFP expression at shield stage (not shown) or bud stage (FIG. 4J) and has no effect on posterior GFP expression (FIG. 4K). One interpretation of this result is that there is no endogenous activation of Wnt/β-catenin target genes in anterior regions of the embryo, and that expression of more posterior genes such as pax2 may be activated by other signals. Alternatively, it is possible that, in the transgenic embryos, the TOPdGFP reporter is unable to respond to Tcf3 signaling due to limiting effects of the insertion into genomic DNA. It is not possible to distinguish between these scenarios, but in either case it is clear that reporter expression is not repressed by hdl function in these fish.

Figure 4L:
Figure 4M:
Figure 4N:
Figure 4O:
Figure 4P:
Figure 4Q:
Figure 4R:
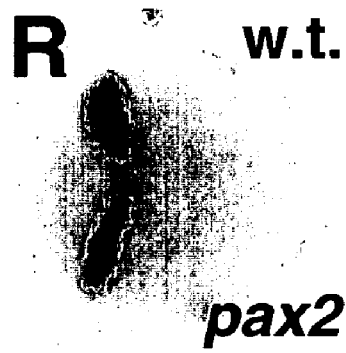
Figure 4S:
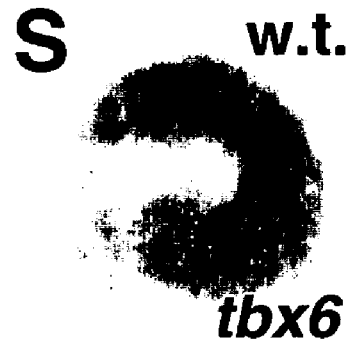
Figure 4T:
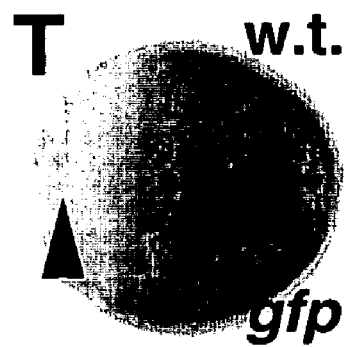
Figure 4U:
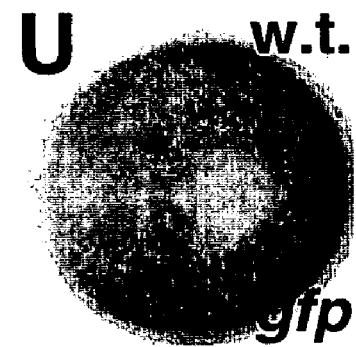

The expression of lef1 suggests that it may be a positive mediator of Wnt-dependent gene activation in the posterior ventrolateral mesoderm. Injection of the lef1 morpholino results in tail truncations and loss of paraxial mesoderm, but normal head development (FIG. 4L). The loss of lef1 has no effect on pax2 expression (FIG.4M), but it results in decreased expression of spt (not shown) and tbx6 (FIG. 4N). This experiment suggests that zebrafish lef1 may play a role analogous to the redundant functions of lef1 and tcf1 in mouse posterior mesoderm development (Galceran et al., 1999). Supporting this hypothesis, no ortholog of tcf1 has been isolated in zebrafish at this point. Following injection of the lef1 morpholino, there is a striking decrease of TOPdGFP expression in the embryo at bud stage (FIGS. 4O and 4P), indicating that this gene is required for the expression of the reporter in vivo. Other work has suggested that ventrolateral mesodermal genes are targets of wnt8 signaling during development (Lekven et al., 2001), and these results provide further evidence for this pathway.

These experiments illustrate an important aspect of TOPdGFP expression in the embryo. The transgene is able to report transcriptional activation mediated by lef1, but not repression mediated by hdl. Because the TOPdGFP construct contains no enhancer elements other than Lef binding sites, it is not surprising that it is inactive even in the absence of repression by hdl. Endogenous Wnt/β-catenin targets may be able to respond to other activating signals in the absence of hdl, due to additional elements controlling their expression. A limitation of the reporter is that it is not confirmed that it reflects all β-catenin-mediated transcription in the embryo. When regions of transgene expression are being examined, it is therefore important to keep in mind that GFP-expressing cells should be considered only as potential sites of β-catenin-activated transcription. However, because early TOPdGFP expression is dependent on Lef1 function, we believe that Lef1/β-catenin signaling is the most likely modulator of this transgene in vivo.

Example 5

Wnt1 is Sufficient to Activate Reporter Expression in vivo

Figure 5A:
FIGS. 5A-5I show that TOPdGFP reporter expression is Wnt-responsive and dynamic throughout development.

Though it was demonstrated that TOPdGFP expression is dependent on lef1 function, the question remained whether the reporter could respond to the entire Wnt signaling pathway. To confirm that a Wnt signal was sufficient to elicit reporter expression, one-cell embryos were injected with a DNA construct encoding myc-tagged Wnt1 under the control of a CMV promoter. Examination of fixed injected embryos at 18 hpf, reveals the detection of coexpression of Wnt1-myc and GFP outside of the endogenous TOPdGFP expression domain (FIG. 5A). GFP expression is not detectable beyond the Wnt-misexpressing cell, which could be due to low levels of misexpression or low sensitivity of the reporter. In addition, not every cell that overexpressed Wnt1 was able to activate TOPdGFP. Again, this could be due to limitations of our reporter, or to the lack of necessary signaling components such as Frizzled receptors at a given location in the embryo. A more rigorous test of the ability of Wnts or other pathway components to activate TOPdGFP may require inducible activation of the pathway throughout the embryo. The current availability of heat-shock transgenic zebrafish (Halloran et al., 2000) will allow such experiments. In addition, it is reasonable to assume that other signaling pathways resulting in Lef1-dependent gene activation could activate the TOPdGFP reporter, such as activation of integrin-linked kinase (Novak et al., 1998). Despite these caveats, the result from this experiment indicates that Wnt signals are capable of activating the TOPdGFP reporter.

Example 6

Dynamic Expression of TOPdGFP in the CNS and other Embryonic Tissues

Figure 5B:
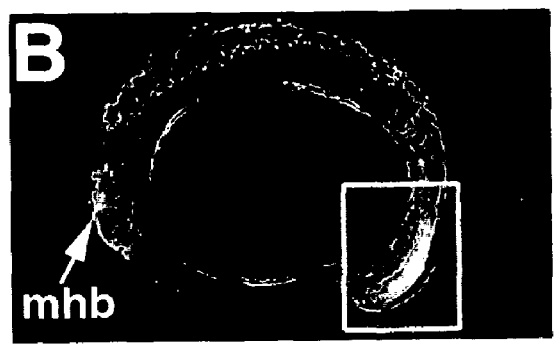
Figure 5C:
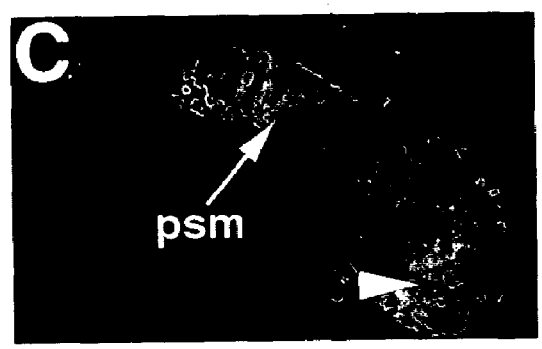
Figure 5D:
Figure 5E:
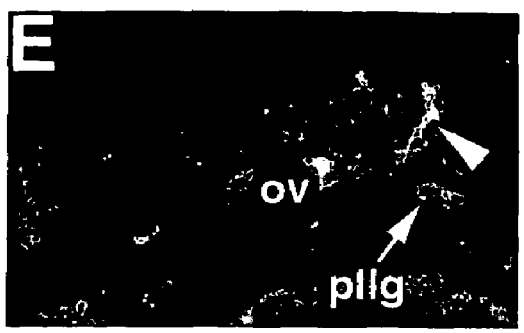
Figure 5F:
Figure 5G:
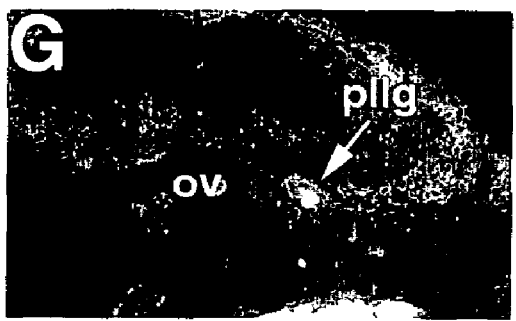
Figure 5H:
Figure 5I:

The TOPdGFP transgenic zebrafish was constructed to characterize novel populations of potential β-catenin-responsive cells in the embryo. As a first step in this analysis, the reporter expression in late embryogenesis was examined focusing primarily on CNS expression-. At 12 hpf, GFP protein expression is observed throughout the CNS and tail mesoderm (FIGS. 5B and 5C). At this stage, a gap in expression exists at the rostral hindbrain, similar to the gap observed in wnt1 and wnt3a expression (Hollyday et al., 1995). In the tail, expression is highest in the presomitic mesoderm, with lingering expression in the newest somites. By 24 hpf, strong expression was observed in the dorsal midbrain, ventral forebrain, eye, ear, and spinal cord (FIG. 5D). Closer examination of the hindbrain region revealed expression in peripheral sensory structures such as the otic epithelium, migrating neural crest, and cranial sensory ganglia (FIG. 5E). These regions of expression persisted at 48 hpf (FIG. 5F), with specific expression in the posterior lateral line ganglion at this stage, when these cells are clearly postmitotic and have extended axons (FIG. 5G). In the spinal cord, many individual neurons that express TOPdGFP appear to have undergone their final differentiation based on their position and morphology (FIG. 5H). Finally, by 72 hpf, the main areas of observable GFP expression were the dorsal midbrain, lens of the eye, and cranial sensory ganglia (FIG. 5I). In summary, TOPdGFP expression undergoes dynamic changes during development from 12 to 72 hpf, disappearing from tail mesoderm and increasing throughout the CNS and sensory ganglia as these cells become postmitotic.

Figure 6A:
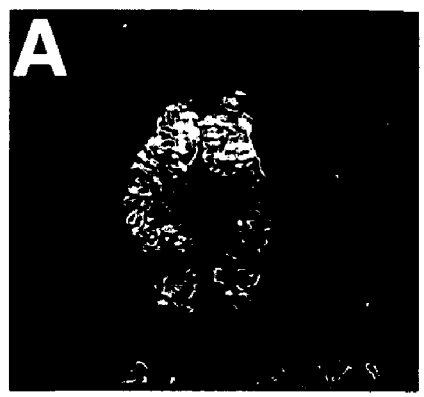
FIGS. 6A-6I show that transverse cryosections of transgenic embryos show localized expression in regions of the CNS and other tissues. In all panels, red autofluorescence is shown for contrast. Spinal cord is outlined in white dotted lines in (FIGS. 6C, 6F, 6I).
Figure 6B:
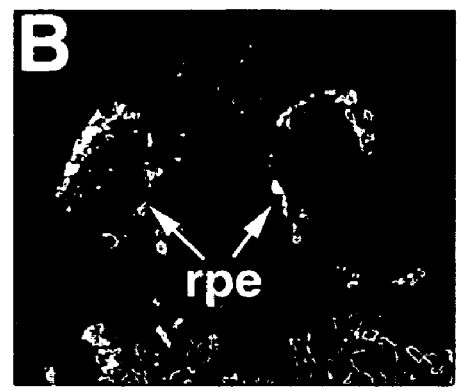
Figure 6C:
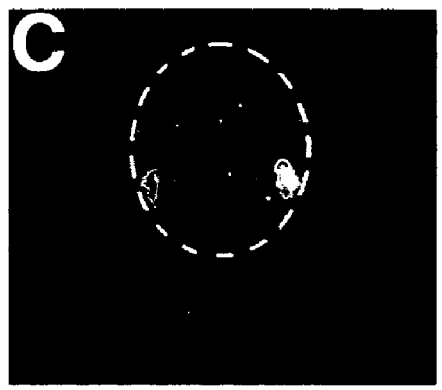
Figure 6D:
Figure 6E:
Figure 6F:
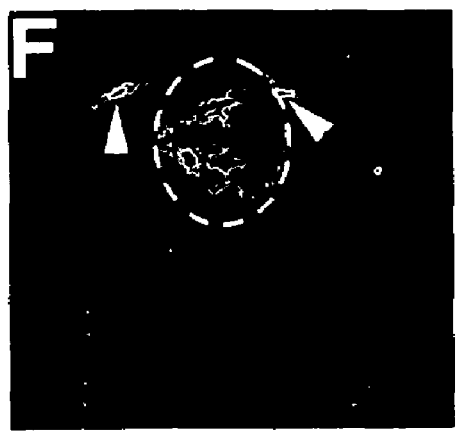
Figure 6G:
Figure 6H:
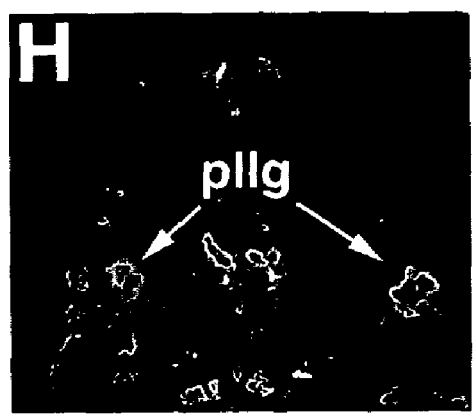
Figure 6I:

To examine the identity of GFP-expressing cells in more detail, fixed embryos were sectioned at multiple developmental stages. At 24 hpf, we observed uniform GFP expression throughout the neuroepithelium of the midbrain (FIG. 6A). In the eye, expression was primarily limited to the retinal pigmented epithelium (RPE), ciliary margin, and lens (not shown), and was absent from the neural retina (FIG. 6B). At this stage, TOPdGFP is strongly expressed in individual spinal neurons (FIG. 6C), a population that has not been previously identified as a Wnt target. By 48 hpf, continued strong expression in the dorsal midbrain and lens is observed, and decreased expression in the RPE and ciliary margin (FIG. 6D). Scattered GFP expression is present at multiple dorsal/ventral positions in the hindbrain (FIG. 6E) and spinal cord (FIG. 6F). In addition, dorsal pigment cells express high levels of the reporter at this stage (FIG. 6F). Sections at 72 hpf confirmed our observations of expression in postmitotic midbrain neurons (FIG. 6G), cranial sensory ganglia (FIG. 6H), and spinal cord neurons (FIG. 6I). Further anatomical and molecular characterization of these populations will be useful in examining possible roles of Wnt/β-catenin signaling in their development.

It should be stressed that TOPdGFP is a reporter of β-catenin signaling, not Wnt activity per se. Potentially, any modulator of Lef1/β-catenin signaling could affect expression of the reporter. As previously mentioned, integrin-linked kinase signaling can activate β-catenin-responsive genes (Novak et al., 1998). In addition, the β-catenin pathway can be negatively regulated by Wnt-independent mechanisms such as p53-mediated induction of Siah (Liu et al., 2001; Matsuzawa and Reed, 2001). Additional Lef/Tcf proteins such as Tcf4 are present in the embryo and their ability to activate the transgene have not been explored. Furthermore, other molecules that can bind to Lef binding sites could regulate TOPdGFP completely independent of Lef1/β-catenin activity. As with any reporter system, unknown mechanisms could be responsible for expression patterns in vivo. While these possibilities cannot be completely ruled out, the above examples show that at least the early expression of the transgene requires Lef1 activity.

It will be appreciated that the methods, fish and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

While the preferred embodiment of the invention has been illustrated and described, it will be appreciated that various changes can be made therein without departing from the spirit and scope of the invention.

BIBLIOGRAPHY

Allen et al. (1988). Transgene as probes for active chromosomal domains in mouse development. *Nature* 33:852-855.

Amsterdam, A. and Hopkins, N. (1999). Retrovirus-mediated insertional mutagenesis in zebrafish. *Methods in Cell Biology* 60:87-98.

Bernhardt, R. R. et al. (1990). Identification of spinal neurons in the embryonic and larval zebrafish. *J Comp. Neurol.* 302:603-616.

Billin, A. N. et al. (2000). Beta-catenin-histone deacetylase interactions regulate the transition of LEF1 from a transcriptional repressor to an activator. *Mol. Cell. Biol.* 20, 6882-6890.

Boutros, M. and Perriman, N. (2002). *Drosophila* Wnt/Fz Pathway, *Science's STKE* (Connections Map, as seen in May 2002), stke.sciencemag.org/cgi/cm/CMP_6459.

Bowerman, B. (2002a). *C. elegans* T Cell Polarity Pathway, *Science's STKE*(Connections Map, as seen May 2002), stke.sciencemag.org/cgi/cm/CMP_10440 (2002a).

Bowerman, B. (2002b). *C. elegans* Gonadogenesis Pathway, *Science's STKE*(Connections Map, as seen May 2002), stke.sciencemag.org/cgi/cm/CMP_10698.

Bowerman, B. (2002c). *C. elegans* Endoderm Induction Pathway, *Science's STKE* (Connections Map, as seen May 2002), stke.sciencemag.org/cgi/cm/CMP_6104.

Bowerman, B. (2002d). *C. elegans* QL Neuroblast Migration Pathway, *Science's STKE* (Connections Map, as seen May 2002), stke.sciencemag.org/cgi/cm/CMP_9763.

Brannon, M. et al. (1999). XCtBP is a XTcf-3 co-repressor with roles throughout *Xenopus* development. *Development* 126, 3159-3170.

Brannon, M. et al. (1997). A beta-catenin/XTcf-3 complex binds to the siamois promoter to regulate dorsal axis specification in *Xenopus. Genes Dev.* 11, 2359-2370.

Bunin et al. (1992). *J. Am. Chem. Soc.* 114:10987.

Burgess, S. and Hopkins, N. (2000). Use of pseudotyped retroviruses in zebrafish as genetic tags. *Methods Enzymol* 327:145-161.

Carell et al. (1994a). *Angew. Chem Int. Ed. Engl.* 33:2059.

Carell et al. (1994b) *Angew. Chem. Int. Ed. Engl.* 33:2061.

Christian, J. L. et al. (1991). Xwnt-8, a *Xenopus* Wnt-1/int-1-related gene responsive to mesoderm-inducing growth factors, may play a role in ventral mesodermal patterning during embryogenesis. *Development* 11, 1045-1055.

Cho et al. (1993). *Science.* 261:1303.

Cull et al. (1992). *Proc Natl Acad Sci USA* 89:1865-1869.

Culp et al. (1991). High-frequency germ-line transmission of plasmid DNA sequences injected into fertilized zebrafish eggs. *Proc. NatL. Acad. Sci. USA* 88:7953-7957.

Cwirla et al. (1990). *Proc. Natl. Acad. Sci. USA* 87:6378-6382.

Devlin (1990). *Science* 249:404-406.

DeWitt et al. (1993). *Proc. Natl. Acad. Sci. USA* 90:6909.

Dickinson, M. E. et al. (1996). Dorsalization of the neural tube by the non-neural ectoderm. *Development* 21, 2099-2106.

Dorsky, R. I. et al. (1998). Control of neural crest cell fate by the Wnt signalling pathway. *Nature* 96, 370-373.

Dorsky, R. I. et al. (1999). Maternal and embryonic expression of zebrafish lef1. *Mech. Dev.* 86, 147-150.

Dorsky, R. I. et al. (2000). Direct regulation of nacre, a zebrafish MITF homolog required for pigment cell formation, by the Wnt pathway. *Genes Dev.* 14, 158-162.

Driever et al. (1996). A Genetic Screen for Mutations Affecting Embryogenesis in Zebrafish *Development* 23:37-46.

Eastman, Q. and Grosschedl, R. (1999). Regulation of LEF-1/TCF transcription factors by Wnt and other signals. *Curr. Opin. Cell Biol.* 11, 233-240.

Erb et al. (1994). *Proc. Natl. Acad. Sci. USA* 91:11422.

Felici (1991). *J Mol. Biol.* 222:301-310.

Fodor (1993). *Nature* 64:555-556.

Galceran, J. et al. (1999). Wnt3a2/2-like phenotype and limb deficiency in Lef1 (2/2)Tcf1 (2/2) mice. *Genes Dev.* 13, 709-717.

Gallop et al. (1994). *J. Med. Chem.* 37:1233.

Golling, G. et al. (2002). Insertional mutagenesis in zebrafish rapidly identifies genes essential for early vertebrate development. *Nat Genet* 31:135-140.

Gong, Y. et al. (2001). *Cell* 107:513.

Gossler et al. (1989). Mouse Embryonic Stem Cells and Reporter Constructs to Detect Developmentally Regulated Genes. *Science* 244:463-465.

Haffter et al. (1996). The identification of genes with unique and essential functions in the development of the zebrafish, Danio rerio. *Development* 23:1-36.

Halloran, M. C. et al. (2000). Laser-induced gene expression in specific cells of transgenic zebrafish. *Development* 27, 1953-1960.

Heasman, J. et al. (1994). Overexpression of cadherins and underexpression of beta-catenin inhibit dorsal mesoderm induction in early *Xenopus* embryos. *Cell* 79, 791-803.

Heikkila, M. et al. (2001). *J. Exp. Zool.* 290:616.

Hinck, L. et al. (1994). *J. Cell Biol.* 124:729.

Hollyday, M. et al. (1995). Wnt expression patterns in chick embryo nervous system. *Mech. Dev.* 52, 9-25.

Horwell et al (1996). *Immunopharmacology* 33:68.

Houghten (1992). *Biotechniques* 13:412-421.

Hug, B. et al. (1997). tbx6, a Brachyury-related gene expressed by ventral mesendodermal precursors in the zebrafish embryo. *Dev. Biol.* 183, 61-73.

Ikeya, M. et al. (1997). Wnt signalling required for expansion of neural crest and CNS progenitors. *Nature* 89, 966-970.

Imai, Y. et al. (2000). Analysis of chromosomal rearrangements induced by postmeiotic mutagenesis with ethylnitrosourea in zebrafish. *Genetics* 155:261-272.

Inoue et al. (1990). Electroporation as a new technique for producing transgenic fish. *Cell. Differ. Develop.* 29:123-128.

Ishikawa, T. et al. (2001). *Development* 28:25.

Kelly, C. et al. (2000). Maternally controlled (beta)-catenin-mediated signaling is required for organizer formation in the zebrafish. *Development* 27, 3899-3911.

Kim, C. H. et al. (2000). Repressor activity of Headless/Tcf3 is essential for vertebrate head formation. *Nature* 407, 913-916.

Kimmel (1989). Genetics and Early Development of Zebrafish. *Trends Genet* 5:283-288.

Korinek, V. et al. (1997). Constitutive transcriptional activation by a beta-catenin-Tcf complex in APC2/2 colon carcinoma. *Science* 275, 1784-1787.

Kothary et al. (1988). A transgene containing lacZ inserted into the dystonia locus is expressed in neural tube. *Nature* 35:435-437.

Krauss, S. et al. (1991). Expression of the zebrafish paired box gene pax[zf-b] during early neurogen-esis. *Development* 13, 1193-1206.

Lam, K. S. (1997). *Anticancer Drug Des.* 12:145.

Lam (1991). *Nature* 54:82-84.

Lekven, A. C. et al. (2001). Zebrafish wnt8 encodes two Wnt8 proteins on a bicistronic transcript and is required for mesoderm and neurectoderm patterning *Dev. Cell* 1, 103-114.

Little, R. D. et al. (2002). *Am. J Hum. Genet.* 70:11.

Liu, J. et al. (2001). Siah-1 mediates a novel beta-catenin degradation pathway linking p53 to the adenomatous polyposis coli protein. *Mol. Cell* 7, 927-936.

Martin, G. (2001). *BioEssays* 23:865.

Matsuzawa, S. I. et al. (2001). Siah-1, SIP, and Ebi collaborate in a novel pathway for beta-catenin degradation linked to p53 responses. *Mol. Cell* 7, 915-926.

McMahon, A P. and Bradley, A. (1990). The Wnt-1 (int-1) proto-oncogene is required for development of a large region of the mouse brain. *Cell* 62, 1073-1085.

Megason, S. G and McMahon, A. P. (2002). *Development* 29:2087.

Moon, R. (020a). Wnt/β-catenin Pathway, *Science's STKE* (Connections Map, as seen in May 2002), http://stke.sciencemag.org/cgi/cm/CMP_5533.

Moon, R. (202b). *Xenopus* Egg Wnt/Beta-Catenin Pathway, *Science's STKE*(Connections Map, as seen May 2002), http://stke.sciencemag.org/cgi/cm/CMP_6031.

Moon, R. et al. (2002) The promise and perils of Wnt signaling through β-catenin. *Science* 296:1644-1646.

Muller et al. (1992). Introducing foreign genes into fish eggs with electroporated sperm as a carrier. *Mol. Mar. Biol. Biotechnol.* 1:276-281.

Muller et al. (1993). Efficient Transient Expression System Based on Square Pulse Electroporation and In Vivo Luciferase Assay of Fertilized Fish Eggs. *FEBS Letters* 324:27-32.

Murakami, et al. (1994). Micromachined electroporation system for transgenic fish. *J Biotechnol.* 34:35-42.

Novak, A. et al. (1998). Cell adhesion and the integrin-linked kinase regulate the LEF-1 and beta-catenin signaling pathways. *Proc. Natl. Acad Sci. USA* 95, 4374-4379.

O'Kane, et al. (1987). Detection in situ of Genomic Regulatory Elements in *Drosophila*. *Proc. Natl. Acad. Sci. USA* 84:9123-9127.

Oxtoby, E. and Jowett, T. (1993). Cloning of the zebrafish krox-20 gene (krx-20) and its expression during hindbrain development. *Nucleic Acids Res.* 21, 1087-1095.

Pelegri, F. and Maischein, H. M. (1998). Function of zebrafish beta-catenin and TCF-3 in dorsoventral patterning. *Mech. Dev.* 77, 63-74.

Polakis, P. (2000). *Genes Dev.* 14:1837.

Riley, B. B. and Grunwald, D. J. (1996). Efficient induction of point mutations allowing recovery of specific locus mutations in zebrafish. *Proc Natl Acad Sci USA* 92:5997-6001.

Roose, J. et al. (1998). The *Xenopus* Wnt effector XTcf-3 interacts with Groucho-related transcriptional repressors. *Nature* 95, 608-12.

Ross, S. E. et al. (2000). *Science* 289:950.

Ryu, S. L. et al. (2001). Regulation of dharma/bozozok by the Wnt pathway. *Dev. Biol.* 231, 397-409.

Schneider, S. et al. (1996). Beta-catenin translocation into nuclei demarcates the dorsalizing centers in frog and fish embryos. *Mech. Dev.* 57, 191-198.

Scott and Smith (1990). *Science* 249:386-390

Sharpe, C. et al. (2001). Wnt signalling: A theme with nuclear variations. *BioEssays* 23, 311-318.

Streisinger (1984). Attainment of Minimal Biological Variability and Measurements of Genotoxicity: Production of Homozygous Diploid Zebra Fish. *Natl. Cancer Inst. Monogr.* 65:53-58.

Symonds, et al. (1994). Electroporation of salmon sperm with plasmid DNA: evidence of enhanced sperm/DNA association. *Aquaculture* 119:313-327.

Szelei, et al. (1994). Liposome-mediated gene transfer in fish embryos. *Transgenic Res.* 3:116-119 (1994).

Taipale, J and Beachy, P. A. (2001). *Nature* 11:349.

Takada, S. et al. (1994). Wnt-3a regulates somite and tailbud formation in the mouse embryo. *Genes Dev.* 8, 174-189.

Turner, D. L. and Weintraub, H. (1994). Expression of achaete-scute homolog 3 in *Xenopus* embryos converts ectodermal cells to a neural fate. *Genes Dev.* 8, 1434-1447.

Waterman, M. L. et al. (1991). A thymus-specific member of the HMG protein family regulates the human T cell receptor C alpha enhancer. *Genes Dev.* 5, 656-669.

Widlund H. R. et al. (2002). *Journal Cell Biol* 158:1079-1087.

Wilkinson, D. G. et al. (1987). Expression of the proto-oncogene int-1 is restricted to specific neural cells in the developing mouse embryo. *Cell* 50:79-88.

Wright, M. et al. (1999). *Biochem. Biophys. Res. Commun.* 263:384.

Zelenin, et al. (1991). The Delivery of Foreign Genes Into Fertilized Fish Eggs Using High-velocity Microprojectiles. *FEBS Letters* 287: 118-120.

Zuckermann. (1994). *J Med Chem.* 37:2678.

U.S. Pat. No. 5,223,409

The invention claimed is:

1. A transgenic zebrafish comprising a reporter nucleic acid comprising a DNA segment consisting of the nucleotide sequence 3005-4336 of SEQ ID NO:1 contiguous to the nucleotide sequence 1-243 of SEQ ID NO:1, wherein said reporter nucleic acid is able to report transcriptional activation by lef1.

2. The transgenic zebrafish of claim 1 which further comprises an induced mutation.

3. The transgenic zebrafish of claim 2, wherein the mutation has been induced by chemical mutagenesis.

4. The transgenic zebrafish of claim 2, wherein the mutation has been induced by insertional retrovirus mutagenesis.

* * * * *

UNITED STATES PATENT AND TRADEMARK OFFICE
CERTIFICATE OF CORRECTION

PATENT NO. : 7,314,968 B2
APPLICATION NO. : 10/679191
DATED : January 1, 2008
INVENTOR(S) : R. T. Moon et al.

It is certified that error appears in the above-identified patent and that said Letters Patent is hereby corrected as shown below:

| COLUMN | LINE | ERROR |
|---|---|---|
| (56) Pg. 2, col. 1 | Refs. Cited (Other Publs., Item 28) | "SO%E2.0/CO%3B2-4>." should read --SO%E2.0.CO%3B2-4>.-- |
| (56) Pg. 2, col. 1 | Refs. Cited (Other Publs., Item 36) | "ARDOCCL%3E2.CO%3B-2-L>." should read --ARDOCCL%3E2.0.CO%3B-2-L>.-- |
| (56) Pg. 2, col. 2 | Refs. Cited (Other Publs., Item 57) | "*128*25-33," should read --*128*:25-33,-- |
| (56) Pg. 2, col. 2 | Refs. Cited (Other Publs., Item 58) | "*127*3899-3911," should read --*127*:3899-3911,-- |
| (56) Pg. 2, col. 2 | Refs. Cited (Other Publs., Item 61) | "Complex a APC\${$^{-1-}$}\$ Colon Carcinoma," should read --Complex in APC$^{-1-}$ Colon Carcinoma,-- |
| (56) Pg. 3, col. 1 | Refs. Cited (Other Publs., Item 79) | "ADISOGR%3E2.0CO%3B2-O>." should read --ADISOGR%3E2.0.CO%3B2-O>.-- |
| (56) Pg. 3, Col. 2 | Refs. Cited (Other Publs., Item 88) | "FPLWA%3ZE2.0.CO%3B2-9>." should read --FPLWA%3E2.0.CO%3B2-9>.-- |
| (56) Pg. 3, col. 2 | Refs. Cited (Other Publs., Item 90) | "ZebraFish,"" should read --Zebra Fish,"-- |
| Pg. 1, col. 2 | Primary Examiner | "Daniel M" should read --Daniel M.-- |

UNITED STATES PATENT AND TRADEMARK OFFICE
CERTIFICATE OF CORRECTION

| | |
|---|---|
| PATENT NO. | : 7,314,968 B2 |
| APPLICATION NO. | : 10/679191 |
| DATED | : January 1, 2008 |
| INVENTOR(S) | : R. T. Moon et al. |

It is certified that error appears in the above-identified patent and that said Letters Patent is hereby corrected as shown below:

| COLUMN | LINE | ERROR |
|---|---|---|
| (57) Pg. 1, col. 2 | Abstract 1 of text | "is directed a" should read --is directed to a-- |

Signed and Sealed this

Twenty-ninth Day of July, 2008

JON W. DUDAS
*Director of the United States Patent and Trademark Office*

SEQUENCE LISTING

<160> NUMBER OF SEQ ID NOS: 4

<210> SEQ ID NO 1
<211> LENGTH: 4336
<212> TYPE: DNA
<213> ORGANISM: Artificial
<220> FEATURE:
<223> OTHER INFORMATION: plasmid
<220> FEATURE:
<221> NAME/KEY: misc_feature
<222> LOCATION: (1)..(1)
<223> OTHER INFORMATION: origin
<220> FEATURE:
<221> NAME/KEY: misc_feature
<222> LOCATION: (38)..(243)
<223> OTHER INFORMATION: SV40 polyA
<220> FEATURE:
<221> NAME/KEY: misc_feature
<222> LOCATION: (3005)..(3374)
<223> OTHER INFORMATION: Topflash enhancer
<220> FEATURE:
<221> NAME/KEY: misc_feature
<222> LOCATION: (3485)..(4327)
<223> OTHER INFORMATION: EGFP+pest

<400> SEQUENCE: 1

| | | | | | |
|---|---|---|---|---|---|
| cctctcgagc | ctctagaact | atagtgagtc | gtattacgta | gatccagaca | tgataagata | 60 |
| cattgatgag | tttggacaaa | ccacaactag | aatgcagtga | aaaaaatgct | ttatttgtga | 120 |
| aatttgtgat | gctattgctt | tatttgtaac | cattataagc | tgcaataaac | aagttaacaa | 180 |
| caacaattgc | attcatttta | tgtttcaggt | tcagggggag | gtgtgggagg | ttttttaatt | 240 |
| cgcggccgcg | gcgccaatgc | attgggcccg | gtacccagct | tttgttccct | ttagtgaggg | 300 |
| ttaattgcgc | gcttggcgta | atcatggtca | tagctgtttc | ctgtgtgaaa | ttgttatccg | 360 |
| ctcacaattc | cacacaacat | acgagccgga | agcataaagt | gtaaagcctg | gggtgcctaa | 420 |
| tgagtgagct | aactcacatt | aattgcgttg | cgctcactgc | ccgctttcca | gtcgggaaac | 480 |
| ctgtcgtgcc | agctgcatta | atgaatcggc | caacgcgcgg | ggagaggcgg | tttgcgtatt | 540 |
| gggcgctctt | ccgcttcctc | gctcactgac | tcgctgcgct | cggtcgttcg | gctgcggcga | 600 |
| gcggtatcag | ctcactcaaa | ggcggtaata | cggttatcca | cagaatcagg | ggataacgca | 660 |
| ggaaagaaca | tgtgagcaaa | aggccagcaa | aaggccagga | accgtaaaaa | ggccgcgttg | 720 |
| ctggcgtttt | tccataggct | ccgcccccct | gacgagcatc | acaaaaatcg | acgctcaagt | 780 |
| cagaggtggc | gaaacccgac | aggactataa | agataccagg | cgtttccccc | tggaagctcc | 840 |
| ctcgtgcgct | ctcctgttcc | gaccctgccg | cttaccggat | acctgtccgc | ctttctccct | 900 |
| tcgggaagcg | tggcgctttc | tcatagctca | cgctgtaggt | atctcagttc | ggtgtaggtc | 960 |
| gttcgctcca | agctgggctg | tgtgcacgaa | ccccccgttc | agcccgaccg | ctgcgcctta | 1020 |

-continued

```
tccggtaact atcgtcttga gtccaacccg gtaagacacg acttatcgcc actggcagca    1080
gccactggta acaggattag cagagcgagg tatgtaggcg gtgctacaga gttcttgaag    1140
tggtggccta actacggcta cactagaagg acagtatttg gtatctgcgc tctgctgaag    1200
ccagttacct tcggaaaaag agttggtagc tcttgatccg gcaaacaaac caccgctggt    1260
agcggtggtt ttttgtttg caagcagcag attacgcgca gaaaaaaagg atctcaagaa    1320
gatcctttga tcttttctac ggggtctgac gctcagtgga acgaaaactc acgttaaggg    1380
attttggtca tgagattatc aaaaaggatc ttcacctaga tccttttaaa ttaaaaatga    1440
agttttaaat caatctaaag tatatatgag taaacttggt ctgacagtta ccaatgctta    1500
atcagtgagg cacctatctc agcgatctgt ctatttcgtt catccatagt tgcctgactc    1560
cccgtcgtgt agataactac gatacgggag ggcttaccat ctggcccag tgctgcaatg    1620 ataccgcgag acccacgctc accggctcca gatttatcag caataaacca gccagccgga    1680
agggccgagc gcagaagtgg tcctgcaact ttatccgcct ccatccagtc tattaattgt    1740
tgccgggaag ctagagtaag tagttcgcca gttaatagtt tgcgcaacgt tgttgccatt    1800
gctacaggca tcgtggtgtc acgctcgtcg tttggtatgg cttcattcag ctccggttcc    1860
caacgatcaa ggcgagttac atgatccccc atgttgtgca aaaagcggt tagctccttc    1920 ggtcctccga tcgttgtcag aagtaagttg gccgcagtgt tatcactcat ggttatggca    1980
gcactgcata attctcttac tgtcatgcca tccgtaagat gcttttctgt gactggtgag    2040
tactcaacca agtcattctg agaatagtgt atgcggcgac cgagttgctc ttgcccggcg    2100
tcaatacggg ataataccgc gccacatagc agaactttaa aagtgctcat cattggaaaa    2160
cgttcttcgg ggcgaaaact ctcaaggatc ttaccgctgt tgagatccag ttcgatgtaa    2220
cccactcgtg cacccaactg atcttcagca tcttttactt tcaccagcgt ttctgggtga    2280
gcaaaaacag gaaggcaaaa tgccgcaaaa aagggaataa gggcgacacg gaaatgttga    2340
atactcatac tcttcctttt tcaatattat tgaagcattt atcagggtta ttgtctcatg    2400
agcggataca tatttgaatg tatttagaaa aataaacaaa tagggggttcc gcgcacattt    2460 ccccgaaaag tgccacctaa attgtaagcg ttaatatttt gttaaaattc gcgttaaatt    2520
tttgttaaat cagctcattt tttaaccaat aggccgaaat cggcaaaatc ccttataaat    2580
caaaagaata daccgagata gggttgagtg ttgttccagt ttggaacaag agtccactat    2640
taaagaacgt ggactccaac gtcaaagggc gaaaaaccgt ctatcagggc gatggcccac    2700
tacgtgaacc atcaccctaa tcaagttttt tggggtcgag gtgccgtaaa gcactaaatc    2760
ggaaccctaa agggagcccc cgatttagag cttgacgggg aaagccggcg aacgtggcga    2820
gaaaggaagg gaagaaagcg aaaggagcgg cgctagggc gctggcaagt gtagcggtca    2880
cgctgcgcgt aaccaccaca cccgccgcgc ttaatgcgcc gctacagggc gcgtcccatt    2940
cgccattcag gctgcgcaac tgttgggaag ggcgatcggt gcgggcctct tcgctattac    3000
gccagtcgag tgaaacataa aatggaatgc aattgttgtt aacttgttta ttgcagctta    3060
taatggttac aaataaagca atagcatcac aaatttcaca ataaagcat tttttttgac    3120 tgcatttcta gttgtggttt gtccaaactc atcaatgtga tcttatcatg tctggatcct    3180
ctagagtcga cctgcagccc aagctatcaa aggggggtaag atcaagggg gtaagatcaa    3240 aggggggtaag atcaaggag gagcttcagt cgaccccagt gacgtaggaa gtccatccat    3300
tcacagcgct tctataaagg cgccagctga ggcgcctact actccaaccg cgactgcagc    3360
gagcaactaa gcttgattta ggtgacacta tagaatacaa gctacttgtt cttttttgcag    3420
```

-continued

```
gatcccatcg attcgaattc tgcagtcgac ggtaccgcgg gcccgggatc caccggtcgc    3480
caccatggtg agcaagggcg aggagctgtt caccggggtg gtgcccatcc tggtcgagct    3540
ggacggcgac gtaaacggcc acaagttcag cgtgtccggc gagggcgagg gcgatgccac    3600
ctacggcaag ctgaccctga agttcatctg caccaccggc aagctgcccg tgccctggcc    3660
caccctcgtg accaccctga cctacggcgt gcagtgcttc agccgctacc ccgaccacat    3720
gaagcagcac gacttcttca agtccgccat gcccgaaggc tacgtccagg agcgcaccat    3780
cttcttcaag gacgacggca actacaagac ccgcgccgag gtgaagttcg agggcgacac    3840
cctggtgaac cgcatcgagc tgaagggcat cgacttcaag gaggacggca acatcctggg    3900
gcacaagctg gagtacaact acaacagcca caacgtctat atcatggccg acaagcagaa    3960
gaacggcatc aaggtgaact tcaagatccg ccacaacatc gaggacggca gcgtgcagct    4020
cgccgaccac taccagcaga acacccccat cggcgacggc cccgtgctgc tgcccgacaa    4080
ccactacctg agcacccagt ccgccctgag caaagacccc aacgagaagc gcgatcacat    4140
ggtcctgctg gagttcgtga ccgccgccgg gatcactctc ggcatggacg agctgtacaa    4200
gaagcttagc catggcttcc cgccggaggt ggaggagcag gatgatggca cgctgcccat    4260
gtcttgtgcc caggagagcg ggatggaccg tcaccctgca gcctgtgctt ctgctaggat    4320
caatgtgtag atgcgc                                                    4336
```

<210> SEQ ID NO 2
<211> LENGTH: 717
<212> TYPE: DNA
<213> ORGANISM: Aequorea victoria
<400> SEQUENCE: 2

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg ccaacactt      180 gtcactactt tctcttatgg tgttcaatgc ttttcaagat acccagatca tatgaaacag     240
catgactttt tcaagagtgc catgcccgaa ggttatgtac aggaaagaac tatattttc     300 aaagatgacg ggaactacaa gacacgtgct gaagtcaagt ttgaaggtga tacccttgtt    360
aatagaatcg agttaaaagg tattgatttt aaagaagatg gaaacattct tggacacaaa    420
ttggaataca actataactc acacaatgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactata caaataa      717
```

<210> SEQ ID NO 3
<211> LENGTH: 25
<212> TYPE: DNA
<213> ORGANISM: Artificial
<220> FEATURE:
<223> OTHER INFORMATION: antisense oligo
<400> SEQUENCE: 3

```
ctcctccacc tgacaactgc ggcat                                            25
```

<210> SEQ ID NO 4

```
<211> LENGTH: 25
<212> TYPE: DNA
<213> ORGANISM: Artificial
<220> FEATURE:
<223> OTHER INFORMATION: antisense oligo

<400> SEQUENCE: 4
ctccgtttaa ctgaggcatg ttggc                                              25
```